US009116151B1

(12) United States Patent
Lim et al.

(10) Patent No.: US 9,116,151 B1
(45) Date of Patent: Aug. 25, 2015

(54) DETECTION PLATE FOR ATP-BIOLUMINESCENCE IMMUNOASSAY AND METHOD OF MANUFACTURING

(71) Applicants: Daniel V. Lim, Tampa, FL (US); Dawn M. Hunter, St. Petersburg, FL (US)

(72) Inventors: Daniel V. Lim, Tampa, FL (US); Dawn M. Hunter, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/952,193

(22) Filed: Jul. 26, 2013

Related U.S. Application Data

(62) Division of application No. 12/767,946, filed on Apr. 27, 2010, now Pat. No. 8,518,658.

(60) Provisional application No. 61/172,854, filed on Apr. 27, 2009.

(51) Int. Cl.
  *C12Q 1/00* (2006.01)
  *C12Q 1/66* (2006.01)
  *G01N 33/569* (2006.01)

(52) U.S. Cl.
  CPC .... *G01N 33/56916* (2013.01); *G01N 33/56938* (2013.01); *G01N 33/56944* (2013.01)

(58) Field of Classification Search
  CPC .............. C12Q 1/68; C12Q 1/00; C12Q 1/66; G01N 33/53; G01N 33/68
  USPC .................. 422/69; 435/7.92, 7.1, 8
  See application file for complete search history.

(56) References Cited

U.S. PATENT DOCUMENTS 5,798,214 A * 8/1998 Squirrell .................. 435/7.4
7,422,868 B2 * 9/2008 Fan et al. .................. 435/29
(Continued)

FOREIGN PATENT DOCUMENTS

EP     441469     * 8/1991 ........... G01N 33/354

OTHER PUBLICATIONS

Almanzar, G et al, Clinical Cancer Research, Mar. 15, 2009, 2009, vol. 15(6), pates 1954-1963, Sperm-Derived SPANX-B is a Clinically Relevant Tumor Antigen That is Expressed in Human Tumors and Readily Recognized by Human CD4+ and CD8+ T cells.*
(Continued)

*Primary Examiner* — Albert Navarro
*Assistant Examiner* — Ginny Portner
(74) *Attorney, Agent, or Firm* — Michele L. Lawson; Smith & Hopen, P.A.

(57) ABSTRACT

Disclosed is a method and associated device for the rapid identification of viable bacterial contaminants in food products. The method detects viable microbes by using a combined ATP-bioluminescence immunoassay. *Escherichia coli* O157:H7 and *Salmonella enterica* serovar *Typhimurium* were selected as target organisms in various matrices including ground beef homogenate, apple juice, milk, and phosphate-buffered saline. Specific antibodies were immobilized on the surface of well plates in which the sample matrices were incubated. The plates were washed, and the wells were incubated with BacTiter-Glo reagent in Mueller-Hinton II broth. Bioluminescent output was measured with a luminometer and signal-to-noise ratios were calculated. The LOD was not affected by the presence of non-target cells. A strong linear correlation was observed between the number of cells and luminescent output over 4 orders of magnitude. This method provides a means of simultaneously detecting and identifying viable pathogens in complex matrices.

8 Claims, 21 Drawing Sheets

(56) References Cited

U.S. PATENT DOCUMENTS

| | | | | |
|---|---|---|---|---|
| 2002/0068309 | A1* | 6/2002 | Schrecengost et al. | 435/8 |
| 2004/0072241 | A1* | 4/2004 | Valkirs et al. | 435/7.1 |
| 2006/0008860 | A1* | 1/2006 | Fan et al. | 435/8 |
| 2006/0129327 | A1* | 6/2006 | Kim et al. | 702/19 |
| 2006/0194223 | A1* | 8/2006 | Andreoli et al. | 435/6 |
| 2006/0286548 | A1* | 12/2006 | Liposky et al. | 435/5 |
| 2007/0020678 | A1* | 1/2007 | Ault-Riche et al. | 435/6 |
| 2007/0054341 | A1* | 3/2007 | Gatto-Menking et al. | 435/7.93 |
| 2007/0224700 | A1* | 9/2007 | Masters | 436/501 |
| 2007/0254320 | A1* | 11/2007 | Olstein | 435/7.32 |
| 2008/0008860 | A1* | 1/2008 | Murray et al. | 428/152 |
| 2008/0057497 | A1* | 3/2008 | Filanoski et al. | 435/6 |
| 2008/0182235 | A1* | 7/2008 | Hearn et al. | 435/5 |
| 2008/0182272 | A1* | 7/2008 | Nagar et al. | 435/7.2 |
| 2008/0241855 | A1* | 10/2008 | Rieunier et al. | 435/7.1 |
| 2008/0311595 | A1* | 12/2008 | Mattsby-Baltzer | 435/7.31 |

OTHER PUBLICATIONS

French, Amanda D et al, International Journal of Medical Sciences, Mar. 12, 2009, vol. 6(2), pp. 93-101, PKC and PKA Phosphorylation Affect the subcellular localization of Claudin-1 Melanoma Cells.*

O' Connell, Michael P. et al, Journal of Investigative Dermatology, 2009, vol. 129, pates 1782-1789, published on line Jan. 29, 2009, Wnt5A Activates the Calpain-Mediated Cleavage of Filamin A.*

Scallan, E. et al. Foodborne Illness Acquired in the United States-Major Pathogens. Emerging Infectious Diseases, vol. 17, No. 1, pp. 7-15, Jan. 2011.

Response to Questions Posed by the Food Safety and Inspection Service Regarding Determination of the Most Appropriate Technologies for the Food Safety and Inspection Service to Adopt in Performing Routine and Baseline Microbiological Analyses. Journal of Food Protection, vol. 73, No. 6, pp. 1160-1200, 2010.

* cited by examiner

Figure 6

| PCR Primers | ipaH-F, ipaH-R, Ent1, Ent2, O157A-F, O157A-R, fliCH7-F, fliCH7-R |
|---|---|
| PCR Mix | Platinum Blue PCR SuperMix |
| PCR Reaction Volume | 50 µl |
| Template Volume | 3 µl |
| Primer Volume | 1 µl |
| Other conditions | 96°C, 56°C, 72°C 30 cycles |
| Gel conditions | 2% agarose gel run at 70 V for 40 minutes, 10 µl loaded |

| Log₁₀ CFU/well | Organism | | |
|---|---|---|---|
| | *E. coli* O157:H7 | *S. sonnei* | Fecal entero-cocci |
| $10^6$ | 18/18 | 18/18 | 10/18 |
| $10^5$ | 18/18 | 18/18 | 10/18 |
| $10^4$ | 12/18 | 15/18 | 5/18 |
| $10^3$ | 9/18 | 9/18 | 0/18 |

Figure 9

DETECTION PLATE FOR ATP-BIOLUMINESCENCE IMMUNOASSAY AND METHOD OF MANUFACTURING

CROSS REFERENCE TO RELATED APPLICATIONS

This application is a divisional application of U.S. Non-Provisional application Ser. No. 12/767,946, filed Apr. 27, 2010, entitled "ATP Bioluminescence Immunoassay", which claims priority to U.S. Provisional Application No. 61/172,854 filed Apr. 27, 2009, each of which is incorporated herein by reference.

GOVERNMENT SUPPORT

This invention was made with government support under grant number W911SR-05-C-0020 and grant account numbers 1209103500, 1209107700 and 1209109711 awarded by the Department of the Army. The government has certain rights in the invention.

BACKGROUND OF THE INVENTION

Rapid, accurate detection methods for pathogenic bacteria are important to the food and dairy industries. Pathogens such as *Escherichia coli* O157:H7 and *Salmonella* spp. are the leading cause of food borne disease outbreaks and cases of known etiology, and have been implicated in outbreaks from consumption of contaminated ground beef, dairy products, and fruit juices. Recent outbreaks illustrate the continued threat bacterial pathogens present to the food supply and consumers. The possibility of contamination postprocessing and at the point of retail sale makes rapid methods vital to consumer safety.

Antibody-based methods such as enzyme-linked immunosorbent assays (ELISA) are commonly used to rapidly detect food borne pathogens such as *E. coli* O157:H7 and *Salmonella* spp., but assay functionality is influenced by environmental factors in the food matrix including pH, salt concentration, and water activity. Enrichment is necessary to overcome matrix effects and to achieve cell concentrations within assay detection limits. Detection by ELISA is specific, but both live and dead cells can elicit an antigenic response. Identification of viable cells is important for the food industry, due to the low infectious doses of *E. coli* O157:H7 and *Salmonella*. Differentiation between live and dead cells can be achieved through bioluminescence assays, which have been used to detect and quantify bacteria in food products including milk, ground beef, produce, and juices. These assays are nonspecific, but have demonstrated more sensitivity than have traditional methods.

A combination of techniques is required to achieve desired sensitivity and specificity and to identify viable cells. Most methods for the detection of viable *E. coli* O157:H7 and *Salmonella* spp. in food products combine immunomagnetic separation (IMS) with culture methods, flow cytometry, or PCR. IMS is designed to concentrate a sample for use in detection assays that have high levels of detection (LOD), but capture efficiency is affected by cell concentration, particulate interference, and nonspecific binding. IMS has also been coupled to fluorescence and chemiluminescence for rapid, specific detection of viable cells in various food matrices. A limited number of IMS bioluminescence assays have been reported, and have primarily been used to demonstrate the efficiency of biosorbents. The efficacy of these assays in complex samples has not been shown.

Bioluminescence assays would have greater utility if viable pathogens could be reliably identified directly from complex matrices. Therefore, what is need is a rapid ATP bioluminescence immunoassay (ATP-BLIA) for detection of viable cells directly from food samples, while maintaining sensitivity and specificity.

SUMMARY OF INVENTION

The problems of the prior art are overcome by the disclosed method, and associated devices, for the detection and quantitation of viable cells as demonstrated using antibodybased biosorbents to separate *Salmonella* and *E. coli* O157:H7 from food samples, which are then subject to a one-step ATP bioluminescence reaction.

The examples set forth below demonstrate an illustrative embodiment for a method for microbial detection by using a combined ATP-bioluminescence immunoassay. *Escherichia coli* O157:H7 and *Salmonella enterica serovar Typhimurium* were selected as target organisms because of their implication in foodborne illness. Various matrices containing the target cells were examined, including ground beef homogenate, apple juice, milk, and phosphate-buffered saline.

In one embodiment, antibodies were immobilized on the surface of 96-well plates, and then the sample matrices containing target cells in the wells were incubated. Sample matrix (no cells) was used to establish background. The plates were washed, and the wells were incubated with BacTiter-Glo reagent in Mueller-Hinton II broth. Bioluminescent output was measured with the GloMax 96 luminometer. Signal-to-noise ratios were calculated, resulting in a limit of detection of 104 CFU/ml for both *E. coli* O157:H7 and *Salmonella Typhimurium*.

The limit of detection for both species was not affected by the presence of nontarget cells. The various sample matrices did not affect signal-to-noise ratios when *E. coli* O157:H7 was the target. A weak matrix effect was observed when *Salmonella Typhimurium* was the target. A strong linear correlation was observed between the number of cells and luminescent output over 4 orders of magnitude for both species. This method, therefore, provides a means of simultaneously detecting and identifying viable pathogens in complex matrices, and could have wider application in food microbiology.

In another embodiment, the invention includes a method of detecting waterborne pathogens using an ATP-BLIA coupled to PCR. The presence of *Escherichia coli* O157:H7, *Shigella sonnei*, and enterococci organisms was confirmed by PCR using DNA obtained after the luminescence assay, and positive detection was obtained at concentrations where the sample may not have been positive in the luminescence assay.

BRIEF DESCRIPTION OF THE DRAWINGS

For a fuller understanding of the invention, reference should be made to the following detailed description, taken in connection with the accompanying drawings, in which:

FIG. 6. Thermal cycling conditions for waterborne pathogen detection.

FIG. 9. PCR detection of waterborne pathogens after an ATP-bioluminescence immunoassay. The concentration refers to the amount incubated in each well for the luminescence immunoassay. Each column displays the total number of positives out of total samples run.

DETAILED DESCRIPTION OF THE PREFERRED EMBODIMENT

Figure 1:
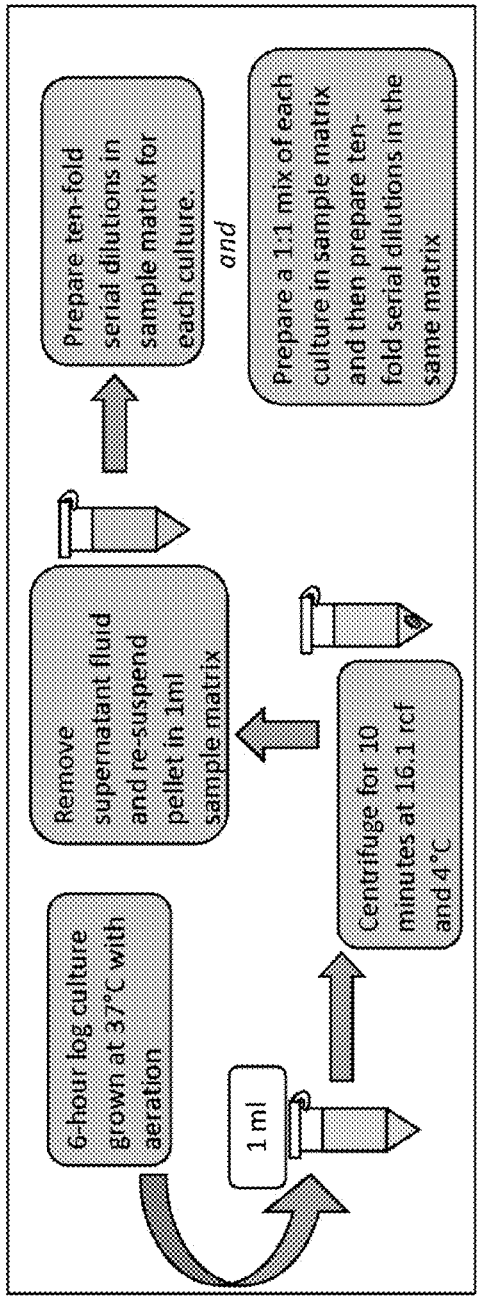
FIG. 1: Preparation of bacterial cultures for use in the immunoassay. Strains used for assay development included *E. coli* O157:H7 ATCC 35150, *S. Typhimurium* ATCC 19585, and *L. monocytogenes* ATCC 7644. The mixed culture contained *E. Coli* O157:H7 and either *S. Typhimurium* (Juice or PBS) or *E. faecalis* (Beef Extract) in assays for the detection of *E. coli* O157:H7. The mixed culture contained *S. Typhimurium* and either *E. coli* O157:H7 (Juice or Beef Extract) or *L. monocytogenes* (Milk) in assays for the detection of *S. Typhimurium*. The mixed culture contained *L. monocytogenes* and either *E. coli* O157:H7, *S. Typhimurium*, or *E. faecalis* (Milk or PBS) in assays for the detection of *L. monocytogene*.

The invention of a general embodiment includes the use of an ATP bioluminescence (ATP-BLIA) assay combined with an immunoassay for simultaneous detection and viability determination. As shown in Examples I-III, viable *Salmonella Typhimurium* and *E. coli* O157:H7 were detected in DPBS, ground beef homogenate, milk, and apple juice, with a level of detection (LOD) 1 log more sensitive than with conventional sandwich ELISA. The ability to distinguish between live and dead cells is important because processing methods may result in nonviable cells that can be detected when using immunoassay alone. ELISA is restricted in both capture and detection by antibody specificity and affinity. ATP-BLIA, however, does not rely on antibodies for the detection step. This significant difference provides an advantage in overcoming matrix effects. In another embodiment, the invention includes a method of detecting of waterborne pathogens using an ATP-BLIA coupled to PCR (see Example IV).

Neither matrix complexity nor the presence of non-targets at nearly equal concentrations affected target pathogen detection in ATP-BLIA. S:N and the spread of the data were comparable within a matrix for any combination of target and non-target. The order of magnitude of S:N was the same across matrices at a given concentration for both *E. coli* O157:H7 and *Salmonella Typhimurium*. The significance of these results is that S:N that fall within a certain range can be correlated to a given cell concentration. This correlation is evident when comparing target cells only versus target cells in mixed culture for both strains—when the concentration is halved, the S:N is approximately halved. This trend was observed in all matrices except apple juice. There was greater variability and higher average S:N for both *E. coli* O157:H7 and *Salmonella Typhimurium* in apple juice, but detection was comparable to the other matrices. Previous research has shown that antibody-based assays for detection in apple juice show reduced sensitivity, but adjustments can be made to the apple juice to reduce variability and improve detection (Nyquist-Battie, C., L. E. Frank, D. Lund, and D. V. Lim. 2004. Optimization of a fluorescence sandwich enzyme-linked immunosorbent assay for detection of *Escherichia coli* O157:H7 in apple juice. J. Food Prot. 67:2756-2759).

ATP-BLIA can detect ≥$10^4$ CFU/ml, but naturally occurring pathogen levels in food samples are typically low. Sample concentration may be required to achieve bacterial numbers within the LOD. In addition, food samples can contain high levels of non-pathogens that can bind nonspecifically to the antibody. Antibody cross-reactivity that is not detectable by ELISA can be detected by ATP-BLIA. However, the ATP-BLIA backgrounds were low regardless of the sample, and ELISA showed specific detection that was unaffected by the presence of non-target cells. These results show one advantage of ATP-BLIA over procedures coupled to IMS, which can capture non-target cells and non-microbial ATP (Ripabelli, G., M. L. Sammarco, and G. M. Grasso. 1999. Evaluation of immunomagnetic separation and plating media for recovery of *Salmonella* from meat. J. Food Prot. 62:198-201; and Wang, X., and M. F. Slavik. 1999. Rapid detection of *Salmonella* in chicken washes by immunomagnetic separation and flow cytometry. J. Food Prot. 62:717-723).

Squirrell et al. (Squirrell, D. J., R. L. Price, and M. J. Murphy. 2002. Rapid and specific detection of bacteria using bioluminescence. Anal. Chim. Acta 457:109-114) reported the efficacy of IMS coupled to bioluminescence, but noted some problems: increased background due to sample complexity, decreased binding efficacy of the target, and the presence of nontarget ATP. These issues have been alleviated in the ATP-BLIA disclosed herein. The advantage of ATP-BLIA is particularly evident in the detection of *Salmonella Typhimurium* in milk, which has been only partially successful when using IMS, due to the clumping of magnetic beads (see Brovko, L. Y., V. G. Froundjian, V. S. Babunova, and N. N. Ugarova. 1999. Quantitative assessment of bacterial contamination of raw milk using bioluminescence. J. Dairy Res. 66:627-631; and Hahm, B. K., and A. K. Bhunia. 2006. Effect of environmental stresses on antibody-based detection of *Escherichia coli* O157:H7, *Salmonella enterica* serotype *Enteritidis* and *Listeria monocytogenes*. J. Appl. Microbiol. 100:1017-1027). Detection of *Salmonella Typhimurium* in milk by using ATP-BLIA was comparable to detection of *Salmonella Typhimurium* in both apple juice and beef homogenate.

Luminescence assays coupled to IMS have been used for rapid, specific detection of viable pathogens, but these assays require enrichment of 6 to 8 hours to improve isolation, and enrichment does not reliably overcome problems associated with complex food samples (American Society for Microbiology. 2005. Rapid detection of *Salmonella* from grocery ready to eat foods. ScienceDaily. Ogden, I. D., M. MacRae, N. F. Hepburn, and N. J. C. Strachan. 2000. Improved isolation of *Escherichia coli* O157 using large enrichment volumes for immunomagnetic separation. Lett. Appl. Microbiol. 31:338-341; and Thompson, T. W., T. P. Stephens, G. H. Loneragan, M. F. Miller, and M. M. Brashears. 2007. Comparison of rapid enzyme-linked immunosorbent assay and immunomagnetic separation methods for detection of *Escherichia coli* O157 in fecal, hide, carcass, and ground beef samples. J. Food. Prot. 70:2230-223). Even when enrichment steps are not used, IMS is restricted by sample volume— larger volumes require increased time to maximize recovery of immunomagnetic beads (Sun, W., F. Khosravi, H. Albrechtsen, L. Y. Brovko, and M. W. Griffiths. 2002. Comparison of ATP and in vivo bioluminescence for assessing the efficiency of immunomagnetic sorbents for live *Escherichia coli* O157:H7 cells. J. Appl. Microbiol. 92:1021-1027).

ATP-BLIA, in contrast, can be completed in 1 hour, from antigen capture through the luminescence assay, by using 96-well plates that previously have been coated with antibody, blocked, and stored. Minimal or no sample pretreatment is involved, and only small volumes of a sample are needed to perform the assay. Pathogen detection with ATP-BLIA was functional across all assay conditions, which is evident in the linear correlation between S:N and cell concentration within each matrix and across matrices for each target. There is a predictable range of S:N proportional to target concentration, which makes it possible to predict the concentration of an unknown but suspected target against known concentrations.

Results shown below were reproducible, with little variability in the data for DPBS, ground beef extract, and pasteurized whole milk. The ATP-BLIA reported here provides consistent, rapid detection and identification of viable pathogens in complex matrices. The possibility exists to adapt this method for use with an even wider variety of food products.

The invention also includes a method combining an ATP bioluminescence immunoassay (ATP-BLIA) and PCR to detect fecal-associated bacteria in concentrated recreational water. Target strains were selected based on their implication in waterborne illness or use as indicator organisms (IOs), and included *Escherichia coli* O157:H7, *Shigella sonnei*, and enterococci.

The specificity of the antibodies was assessed by ELISA prior to their use in the ATP-bioluminescence immunoassay. All three were specific for their respective targets with minimal to no cross-reactivity noted except at very high concentrations of non-target cells. The limit of detection in the luminescence assay was $10^4$ CFU/ml for *E. coli* O157:H7, $10^5$ CFU/ml for *S. sonnei*, and $10^6$ CFU/ml for the enterococci. The presence of all three organisms was confirmed by PCR using DNA obtained after the luminescence assay, and positive detection was obtained at concentrations where the sample may not have been positive in the luminescence assay.

Rapid and accurate detection of microbial pathogens is necessary to reduce the incidence of illnesses from contamination of public water sources. Specific detection of live *E. coli* O157:H7, *S. sonnei*, and fecal enterococci using the ATP-bioluminescence immunoassay occurred within 4 hours and was not affected by the presence of fecal coliforms and *E. coli* at high concentrations in the concentrated sample.

EXAMPLES

The following materials and methods where used for Examples I-III:

ATP-BLIA Antibodies: Lyophilized, affinity-purified, goat polyclonal antibody to *E. coli* O157:H7 Kirkegaard and Perry Laboratories, Inc., Gaithersburg, Md.) and affinity-purified, rabbit polyclonal antibody to *Salmonella* group antigen in PBS (AbD Serotec, Serotec, Inc., Raleigh, N.C.) were used as capture antibodies in the ATP-BLIA.

ELISA Antibodies: Lyophilized, affinity-purified, goat polyclonal antibody to *E. coli* O157:H7 conjugated to horseradish peroxidase (Kirkegaard and Perry Laboratories, Inc.) and affinity-purified, rabbit polyclonal antibody to *Salmonella* group antigen conjugated to horseradish peroxidase in PBS (AbD Serotec) were used as detection antibodies in ELISA. The lyophilized *E. coli* antibodies were rehydrated by addition of a 50% glycerol solution.

Bacterial strains and culture conditions (FIG. 1): Capture antibodies were evaluated by ELISA employing the bacteria listed in Table 1, grown for 18 hours at 37° C. on tryptic soy agar (TSA; Difco, Becton Dickinson, Sparks, Md.) plates. *E. coli* O157:H7 (ATCC 35150), *Salmonella Typhimurium* (ATCC 19585), *Enterococcus faecalis* (ATCC 19433), and *Listeria monocytogenes* (ATCC 7644) were used as test organisms in the ATP-BLIA. Subsequent evaluation of additional strains by ATP-BLIA was performed with the bacteria listed in Table 1. Working stocks were made from frozen cultures grown for 18 h at 37 uC in Mueller Hinton II (MHII) broth. Stocks were maintained at 4° C. for up to 30 days and were regularly checked for purity by microscopic examination. One hundred micro-liters of stock was transferred to 5 ml of MHII broth and incubated for 18 hours at 37° C.; 100 ml was then transferred to 5 ml of MHII broth and incubated for 6 h at 37° C. Cells from this culture were pelleted by centrifugation (16,100×g for 10 min at 4° C.) in a micro-centrifuge (5415R, Eppendorf North America, Westbury, N.Y.), the supernatant fluids removed, and pellets suspended in 1 ml of sample matrix. Individual suspensions were serially diluted (1:10) in sample matrix. A 1:1 mixture of target to non-target bacteria in sample matrix was also prepared and serially diluted (1:10). Mixed cultures were prepared with bacteria considered likely to be found in a given matrix (Lynch, M., J. Painter, R. Woodruff, and C. Braden. 2006. Surveillance for foodborne-disease outbreaks—United States, 1998-2002. MMWR Surveill. Summ. 55:1-34; Stiles, M. E., and L. Ng. 1981. Enterobacteriaceae associated with meats and meat handling. Appl. Environ. Microbiol. 41:867-872; and Vodjani, J. D., L. R. Beuchat, and R. V. Tauxe. 2008. Juiceassociated outbreaks of human illness in the United States, 1995 through 2005. J. Food Prot. 71:356-364).

Mixed cultures contained *E. coli* O157:H7 and either *Salmonella Typhimurium* (apple juice, phosphate-buffered saline [PBS], and beef homogenate), *E. faecalis* (beef homogenate), or *L. monocytogenes* (PBS) in assays for the detection of *E. coli* O157:H7. Mixed cultures contained *Salmonella Typhimurium* and either *E. coli* O157:H7 (apple juice, milk, or beef homogenate) or *L. monocytogenes* (milk) in assays for the detection of *Salmonella Typhimurium*.

Sample matrices: Pasteurized apple juice and whole milk, 96% lean ground beef, and 0.01 M Dulbecco's PBS (DPBS; pH 7.4) were inoculated with different concentrations of *E. coli* O157:H7, *Salmonella Typhimurium*, or mixed cultures. Inoculum levels were determined by total viable counts on TSA incubated at 37° C. for 18 hours. Total viable counts for ground beef homogenate were completed on the DPBS inoculum added to the beef prior to homogenization, due to high background flora in the beef.

Table 1

| Bacterium | Source of strain[a] | Elisa | ATP-BLIA |
|---|---|---|---|
| *Citrobacter freundii* | ATCC 8090 | ✓ | ✓ |
| *Enterococcus faecalis* | ATCC 19433 | ✓ | ✓ |
| *Enterococcus faecium* | ATCC 19434 | ✓ | |
| *Escherichia coli* | ATCC 25922 | ✓ | ✓ |
| *E. coli* O126:H27 | CDC5194-55 | ✓ | |
| *E. coli* O157:H7 | Mass. DOH (2 strains) | ✓ | ✓ |
| | CBD 1171, 1178, 1183, 1191 | ✓ | ✓ |
| | CBD 1203, 1211 | ✓ | |
| | ATCC 35150 | ✓ | ✓ |
| | ATCC 43895 | ✓ | |
| | ATCC 43888 | | ✓ |
| *E. coli* O157:NM | ATCC 700375 | | ✓ |
| *Listeria monocytogenes* | ATCC 7644 | ✓ | ✓ |
| *Pseudomonas aeruginosa* | ATCC 15442 | ✓ | ✓ |
| *Salmonella choleraesuis* | ATCC 10708 | ✓ | ✓ |
| *Salmonella Enteritidis* | ATCC 31194 | ✓ | |
| | CBD 0781, 0818, 1060, 1291 | ✓ | ✓ |
| | CBD 0439, 0779, 0832 | ✓ | |
| *Salmonella* Hadar | ATCC 51956 | ✓ | |
| *Salmonella* Kentucky | ATCC 9263 | ✓ | |
| *Salmonella* Newport | ATCC 27896 | ✓ | |
| | CBD 0213, 0425, 0427 | ✓ | |
| *Salmonella Typhimurium* | ATCC 19585, 14028 | ✓ | ✓ |
| | ATCC 23564 | ✓ | |
| | CBD 0757, 0775, 0778, 0817 | ✓ | ✓ |
| | CBD 0820, 0828 | ✓ | |
| | USF-MC | ✓ | ✓ |
| | WARD's | ✓ | |
| *Shigella flexneri* | ATCC 12022 | ✓ | |
| *Shigella sonnei* | ATCC 25931 | ✓ | |

[a]ATCC, Americal Type Culture Collection, CDC, Centers for Disease Control and Prevention (Atlanta, GA); Mass. DOH, Massachusetts Department of Health (Jamaica Plains, NY); CBD, University of South Florida Center for Biological Defense (Tampa, FL); USF-MC, University of South Florida Medical Clinics (Tampa, FL); WARD's, WARD's Natural Science (Rochester, NY).

Homogenate was prepared by adding 1 ml of the test organism(s) in DPBS to 10 g of beef in 50-ml conical tubes. This mixture was supplemented with 30 ml of DPBS after 10 to 15 min, and the slurry was homogenized with a PowerGen 125 homogenizer (Fisher, Pittsburgh, Pa.) for 10 seconds. The homogenate was centrifuged (500×g for 5 min at 4 uC) in a Beckman Alegra 6R (Beckman Coulter, Brea, Calif.) to form three layers. The pathogen-containing middle layer was removed and transferred to 15-ml conical tubes for use in the ATP-BLIA. Apple juice was adjusted to pH 7.4±0.1 prior to inoculation. No additional preparation was needed prior to the inoculation of milk or DPBS. All matrices were evaluated for total coliforms, *E. coli* O157:H7, and *Salmonella* spp., as described in the U.S. Food and Drug Administration's Bacteriological Analytical Manual. Confirmatory testing was completed with CHROMagar O157 (BBL, Becton Dickinson, Sparks, Md.) and API 20E tests strips (bioMerieux, Inc., Hazelwood, Mo.).

Samples can alternatively be prepared by dead-end hollow fiber ultrafiltration using the USF patent-pending manual or automated concentration system developed in the Lim laboratory. Samples prepared in this manner can include natural recreational water from local locations as well as spinach and lettuce wash. The samples are spiked with target cells (*E. coli* O157:H7), grown overnight on TSA and suspended in a buffer such as phosphate-buffered saline (PBS). It is important that the spinach or lettuce is washed since it is the wash that is concentrated. Large volume samples (10-100 L) are vacuum filtered, and the filter is then backflushed with an elution buffer. The backflushed sample, or "retentate," is a smaller volume sample (less than 250 mL). The retentate is then secondarily concentrated using either a manual or automated filtration system, further reducing the total volume to less than 5 mL. This secondary retentate is then used in the ATP-BLIA and has been used in IMS-bioluminescence assays.

A third method of sample preparation includes whole blood processing. In this method, target cells (*S. aureus*) are grown overnight on BHI agar and suspended in a buffer such as phosphate-buffered saline (PBS). Citrated whole sheep blood is diluted with ACD buffer and spiked with target cells or blanks (PBS without cells). The blood is centrifuged for 10 min at 10000×g at 23° C. Serum is decanted and the pellet is re-suspended in 10 ml of lysis solution and incubated for 30 min at 23° C. The sample is centrifuged again for 10 min at 10000×g at 23° C. and the serum is decanted. The pellet (which contains the target cells, if present) is re-suspended in broth or buffer for use in the ATP-BLIA or IMS-bioluminescence assays.

Figure 2:
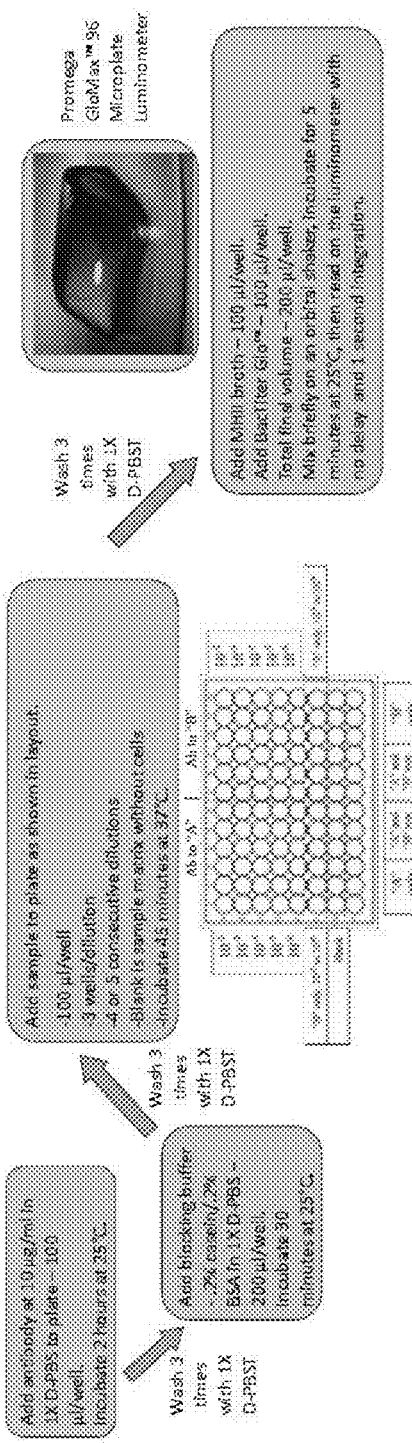
FIG. 2: ATP bioluminescence immunoassay on the Glo-Max™ 96 Microplate Luminometer. Capture antibody is either KPL Goat anti-*E. coli* O157:H7, AbD Serotec Rabbit anti-*Salmonella* Group Antigen, or AbD Serotec Mouse anti-*Listeria monocytogenes*. D-PBS was 0.01 M Dulbecco's formulation phosphate buffered saline. MHII broth was used to measure luminescent output because of its low luminescence background. The BacTiter-Glo™ reagent was reconstituted and equilibrated to room temperature at least two hours prior to use. Plates for all assays were Lumitrac™ 200 opaque white 96-well plates. The same general plate layout was followed for all assays, the only exception being that the $10^{-1}$ to $10^{-5}$ dilutions were used for samples spiked with *L. monocytogenes*.

ATP-BLIA (FIG. 2): Lumitrac 200 96-well plates (ISC Bioexpress, Kaysville, Utah) were coated with capture antibody (100 µl per well) at 10 µg/ml in DPBS and incubated at 23° C. for 2 hours. Plates were washed three times with DPBS containing 0.05% Tween 20, with a microplate strip washer (ELx50, BioTek Instruments, Inc., Winooski, Vt.), and then blocked with 200 µl per well of blocking buffer (0.2% casein, and 0.2% bovine serum albumin in DPBS) for 30 minutes at 23° C. Plates were washed again, and consecutive serial dilutions of sample matrix containing target cells or a mixed culture were added in triplicate (100 µl per well) and incubated for 45 minutes at 37° C. Background was established with a minimum of 6 wells containing non-spiked matrix. Plates were washed, MHII broth was added (100 µl per well), and then BacTiter-Glo reagent (bioluminescence reagent comprising an ATP extracting agent and Luciferase enzyme) (Promega, Madison, Wis.) was added (100 µl per well). Contents of the plate were mixed briefly on an orbital shaker, incubated for 5 minutes at 23° C., and read on a GloMax 96 microplate luminometer (Promega), with no delay and 1-s integration. The assay was performed with *E. coli* O157:H7 and BacTrace *Salmonella Typhimurium* Positive Control (heat-killed cells; Kirkegaard and Perry Laboratories, Inc.) in DPBS to determine specificity for live cells. Cell suspensions were serially diluted (1:10), and consecutive dilutions were tested in triplicate, using DPBS to establish background.

Raw luminescence signals in relative light units (RLU) were averaged after the elimination of outliers to determine background, and standard deviations were calculated. The upper and lower limits for outliers were determined with the fourth spread, and were considered values 1.5 times the fourth spread above and below the median. Triplicate signal values for each concentration were averaged. S:N were calculated as the average signal minus the average background divided by the standard deviation of the background. Average S:N≥3.0 were considered positive.

ELISA: Cells were suspended and serially diluted in DPBS. A 1:1 (vol:vol) mixture of $E.$ $coli$ O157:H7 and $Salmonella$ $Typhimurium$ was also prepared and serially diluted (1:10). Triplicate assays were performed in MaxiSorp 96-well plates (Nalge Nunc International, Rochester, N.Y.). Consecutive serial dilutions were added to the plates in triplicate (100 µl per well) and incubated for 45 minutes at 37° C. Plates were washed three times with 100 ml of DPBS containing 0.05% Tween 20, and then blocked with 200 µl of blocking buffer per well for 30 min at 23 uC. Plates were washed and then coated with 100 µl of either horseradish peroxidase-labeled antibody to $E.$ $coli$ (0.5 mg/µl in DPBS) or $Salmonella$ (2.5 µg/ml in DPBS) and incubated at 23° C. for 30 minutes. Antibody concentrations were determined by titration. DPBS was used to establish background. Plates were washed a final time, and peroxidase activity was detected with the QuantaBlu fluorogenic peroxidase substrate kit (Pierce, Rockford, Ill.) and then analyzed with a Spectra-Max Gemini XS spectrofluorometer (Molecular Devices, Sunnyvale, Calif.) with the following parameters: 340-nm excitation, 470-nm emission, 455-nm cutoff, and the photomultiplier tube was set to "Auto." S:N were determined by dividing raw fluorescence by average background fluorescence. Triplicate S:N from triplicate plates were averaged, and standard deviations were calculated. Average S:N≥2.0 were considered positive.

Statistical analysis: Average S:N generated by each concentration of the target organism in each matrix for the ATP-BLIA were compared by linear regression (GraphPad InStat 3, GraphPad Software, Inc., San Diego, Calif.). The coefficient of determination ranges from 0 to 1, with values close to 1 indicating that the variance in x can be strongly attributed to y. Values close to 1 for ATP-BLIA indicate that the variation in S:N can be attributed to cell concentration. Differences in S:N across matrices for each target at a given concentration were analyzed with Kruskal-Wallis one-way analysis of variance with Dunn's multiple comparisons posttest (multiple groups) or the Mann-Whitney test (two groups) because of non-Gaussian distributions among some groups of data that were not resolved by log transformation (GraphPad InStat 3). Differences in S:N across concentrations for each target in a given matrix were analyzed with the Mann-Whitney test (GraphPad InStat 3). Differences were considered statistically significant for P being equal to or less than 0.05 (95% confidence level).

Example I

Sample Analysis

Apple juice, milk, and ground beef were analyzed for the presence of viable organisms prior to inoculation. The apple juice and milk were free of contaminants. Analysis of the ground beef by the most probable-number (MPN) technique for total coliforms resulted in an average of 9.2 MPN/g. Additional analyses with CHROMagar O157 and API 20E tests strips revealed that the beef did not contain $E.$ $coli$ O157:H7 or $Salmonella$.

Example II

ELISA

The sensitivity and specificity of the $Salmonella$ and $E.$ $coli$ antibodies were evaluated by ELISA. Positive detection (S:N≥2.0) of $Salmonella$ $Choleraesuis$, one $Salmonella$ $Enteritidis$, and six $Salmonella$ $Typhimurium$ strains occurred at $10^5$ CFU/ml. There was also detection of four $Salmonella$ $Typhimurium$ strains at $10^6$ CFU/ml; two strains of $Salmonella$ $Enteritidis$ at $10^6$ CFU/ml and five strains at $10^7$ CFU/ml; and $Salmonella$ Hadar, $Salmonella$ Kentucky, and two $Salmonella$ Newport strains at 108 CFU/ml. Positive detection of all $E.$ $coli$ O157:H7 strains occurred at $10^5$ CFU/ml. Both antibodies were nonreactive to the other organisms evaluated at all concentrations. Detection of the target strains was not affected by the presence of non-target cells.

Example III

ATP-BLIA

Immunocapture and detection of live $E.$ $coli$ O157:H7 in PBS, beef homogenate, and apple juice, and live $Salmonella$ $Typhimurium$ in beef homogenate, apple juice, and whole milk were demonstrated with ATP-BLIA. The LOD was determined by assessing significant differences in mean S:N≥3.0 RLU across concentrations for each matrix. Direct cell counts could not be completed prior to the assay, due to the background present in some samples, which resulted in assay-to-assay variability in cell concentration. The reported values are averages of total viable counts across all assays.

Figure 3:
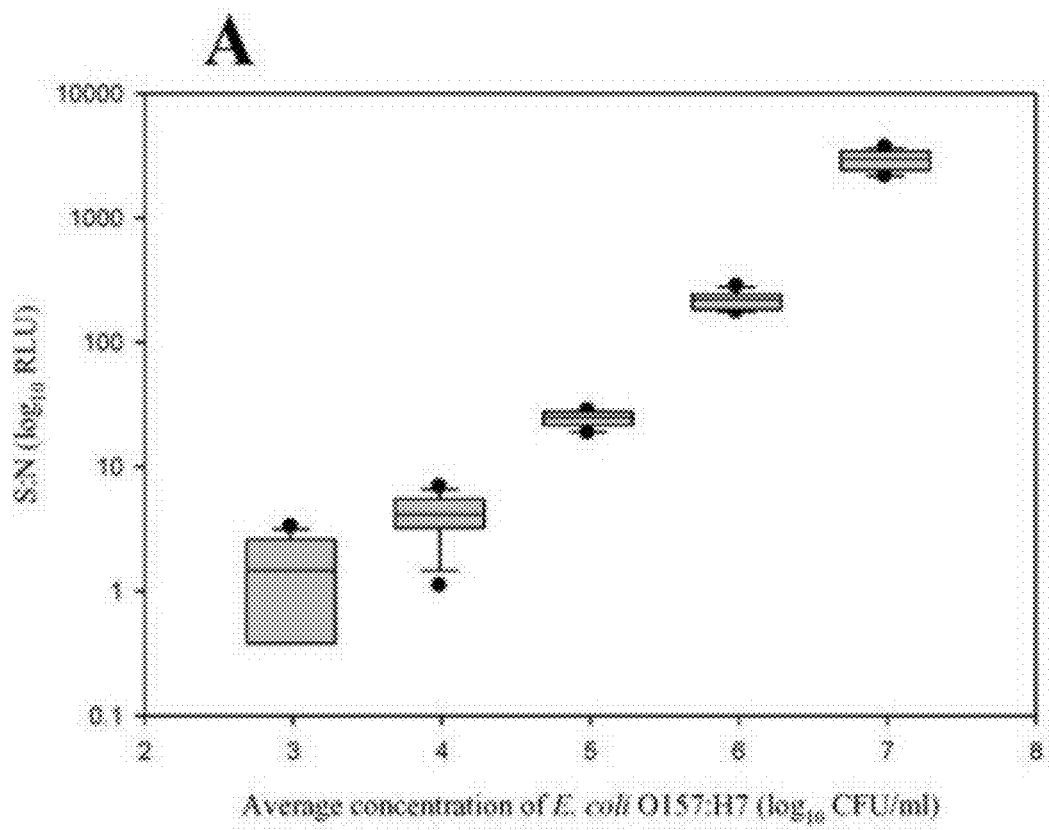
FIG. 3. Comparison of the S:N ratios generated by different concentrations of *Escherichia coli* O157:H7 in each matrix by using ATP-BLIA. (A) PBS with target cells only, (B) PBS with target cells in mixed culture, (C) ground beef homogenate with target cells only, (D) ground beef homogenate with target cells in mixed culture, (E) pasteurized apple juice with target cells only, and (F) pasteurized apple juice with target cells in mixed culture. Each box displays the range of S:N values for each cell concentration and includes the median value as well as the 25th and 75th percentiles (lower and upper box limits, respectively). Error bars represent the 10th and 90th percentiles of the data.
Figure 3:
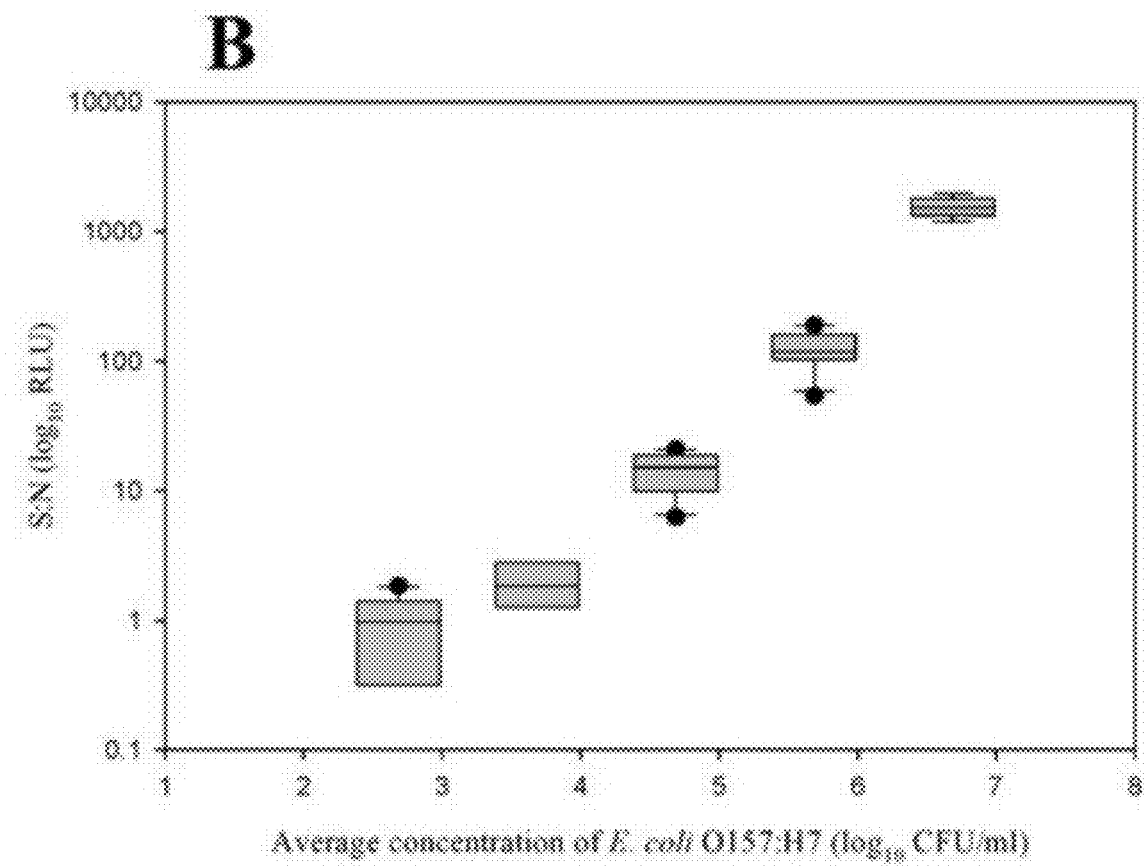
Figure 3:
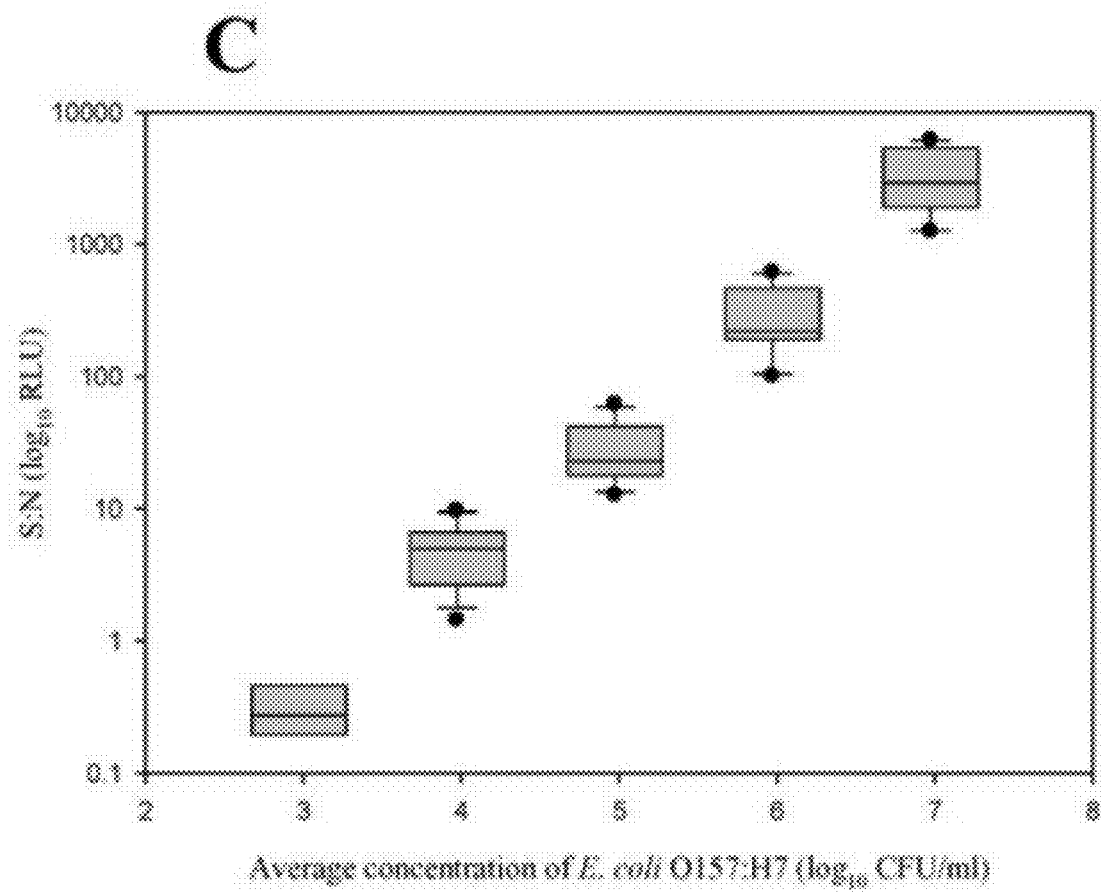
Figure 3:
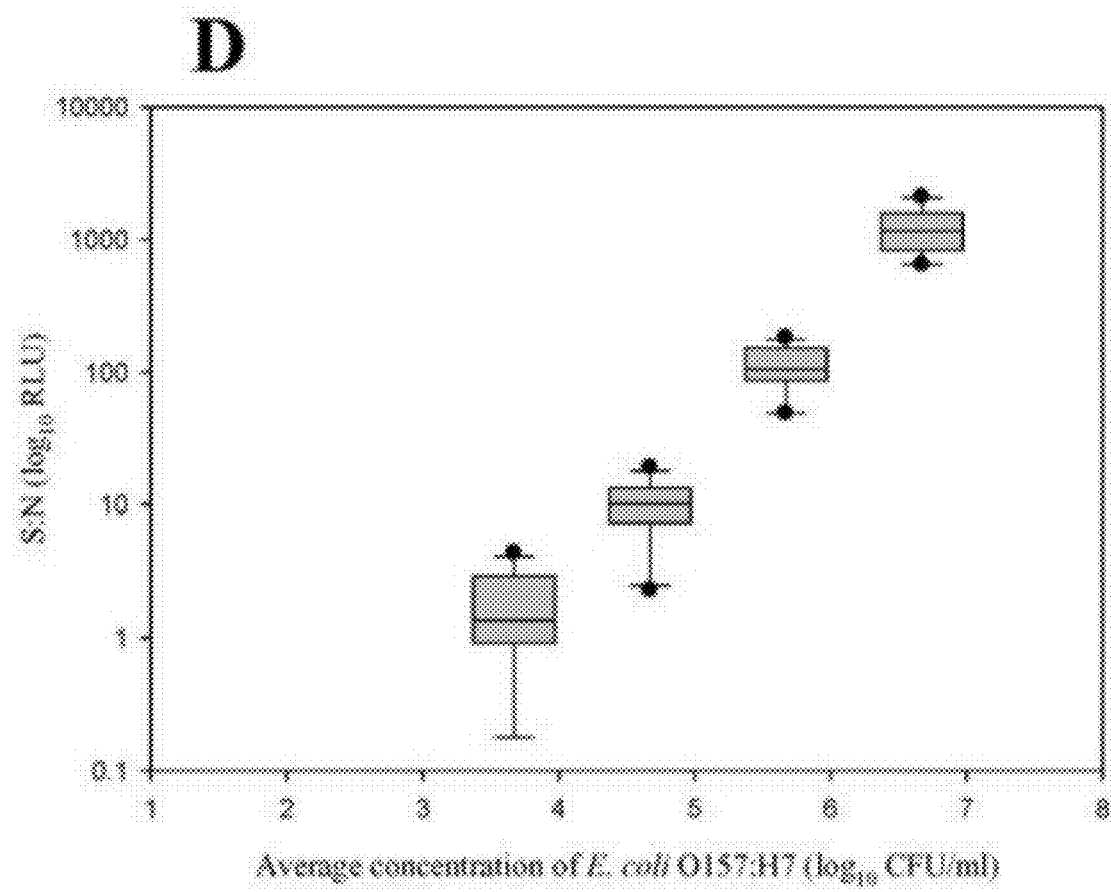
Figure 3:
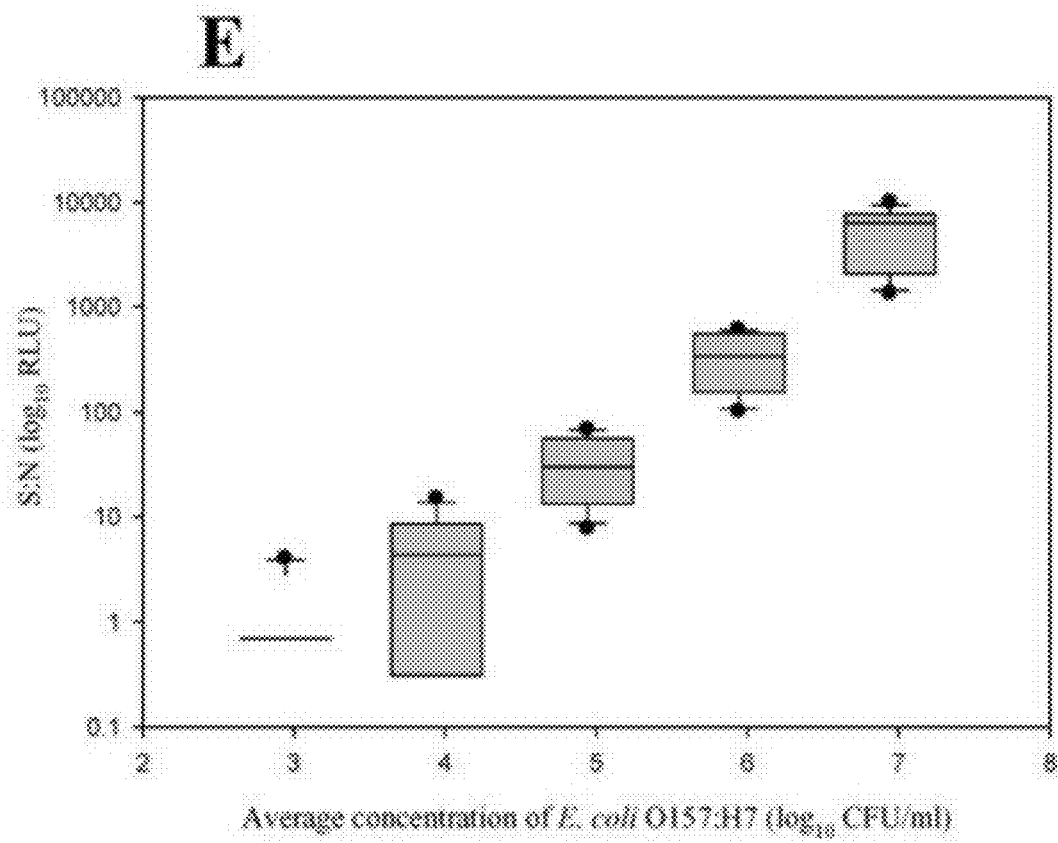
Figure 3:
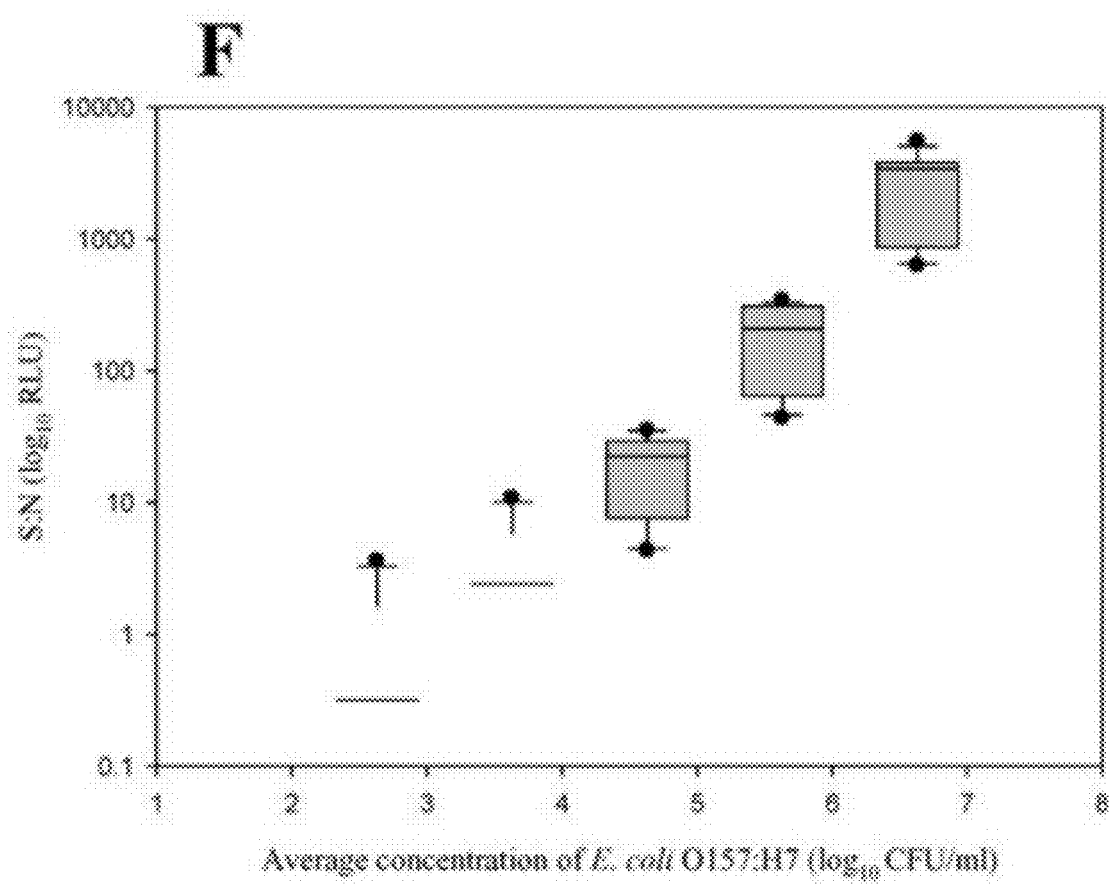

The LOD for $E.$ $coli$ O157:H7 in DPBS (n=12) was $9.68 \times 10^3$ CFU/ml for the target only (FIG. 3A) and $4.84 \times 10^4$ CFU/ml in mixed culture (FIG. 3B). There was no overlap of average S:N at concentrations>$10^4$ CFU/ml. There was also little variability within both sets of data for this matrix. S:N were significantly higher at all concentrations when comparing $E.$ $coli$ O157:H7 only to $E.$ $coli$ O157:H7 in mixed culture (P<0.0001 at all concentrations≥$10^4$ CFU/ml).

Figure 4:
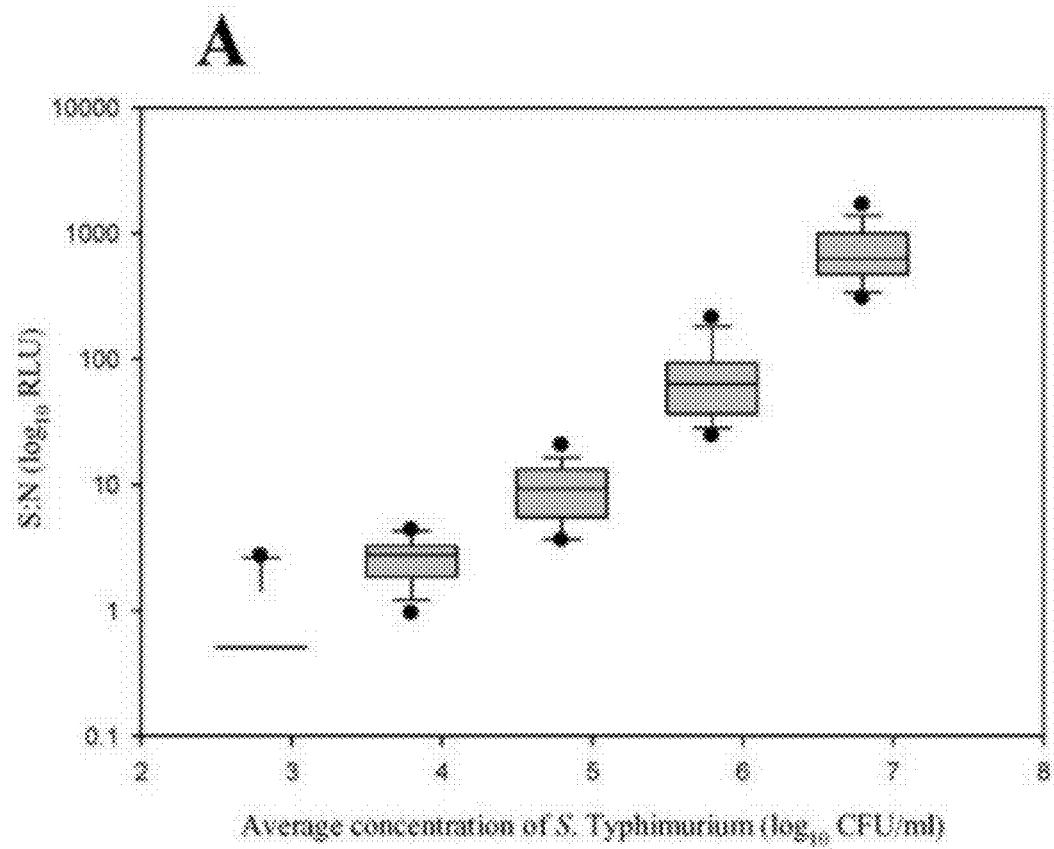
FIG. 4. Comparison of the S:N ratios generated by different concentrations of *Salmonella Typhimurium* in each matrix by using ATPBLIA. (A) Ground beef homogenate with target cells only, (B) ground beef homogenate with target cells in mixed culture, (C) pasteurized apple juice with target cells only, (D) pasteurized apple juice with target cells in mixed culture, (E) pasteurized whole milk with target cells only, and (F) pasteurized whole milk with target cells in mixed culture. Each box displays the range of S:N values for each cell concentration and includes the median value as well as the 25th and 75th percentiles (lower and upper box limits, respectively). Error bars represent the 10th and 90th percentiles of the data.
Figure 4:
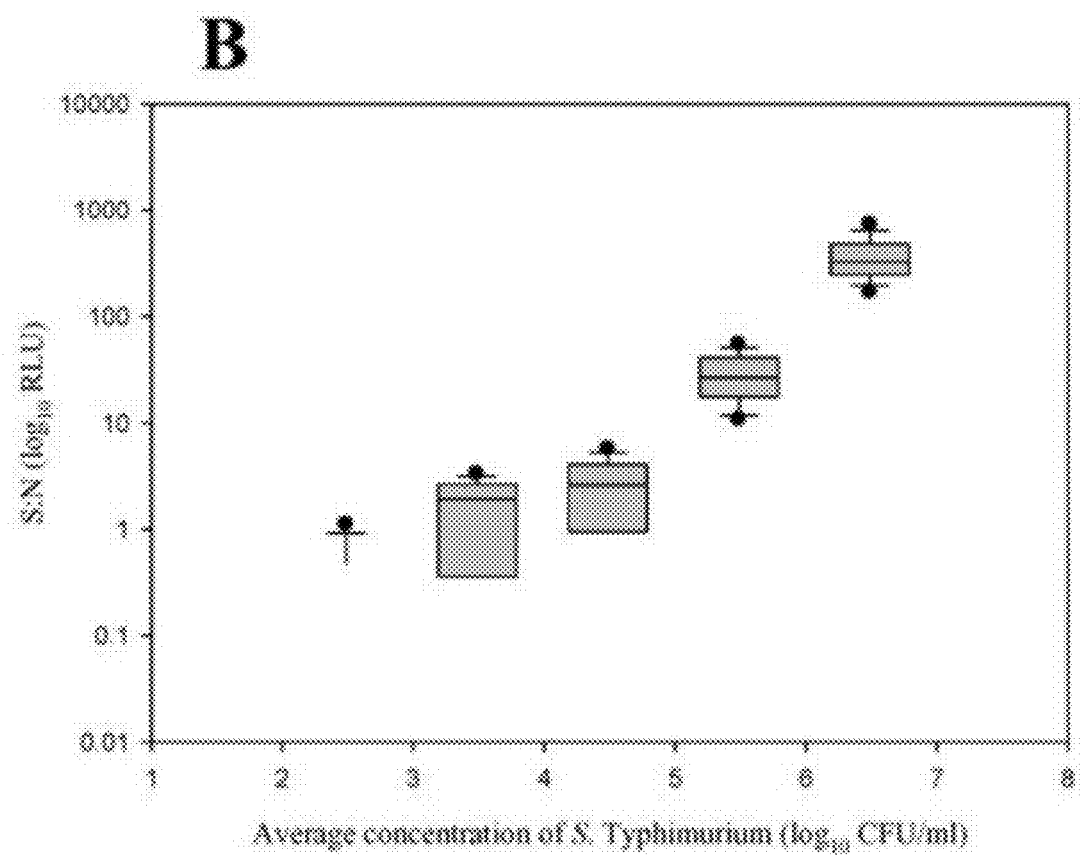
Figure 4:
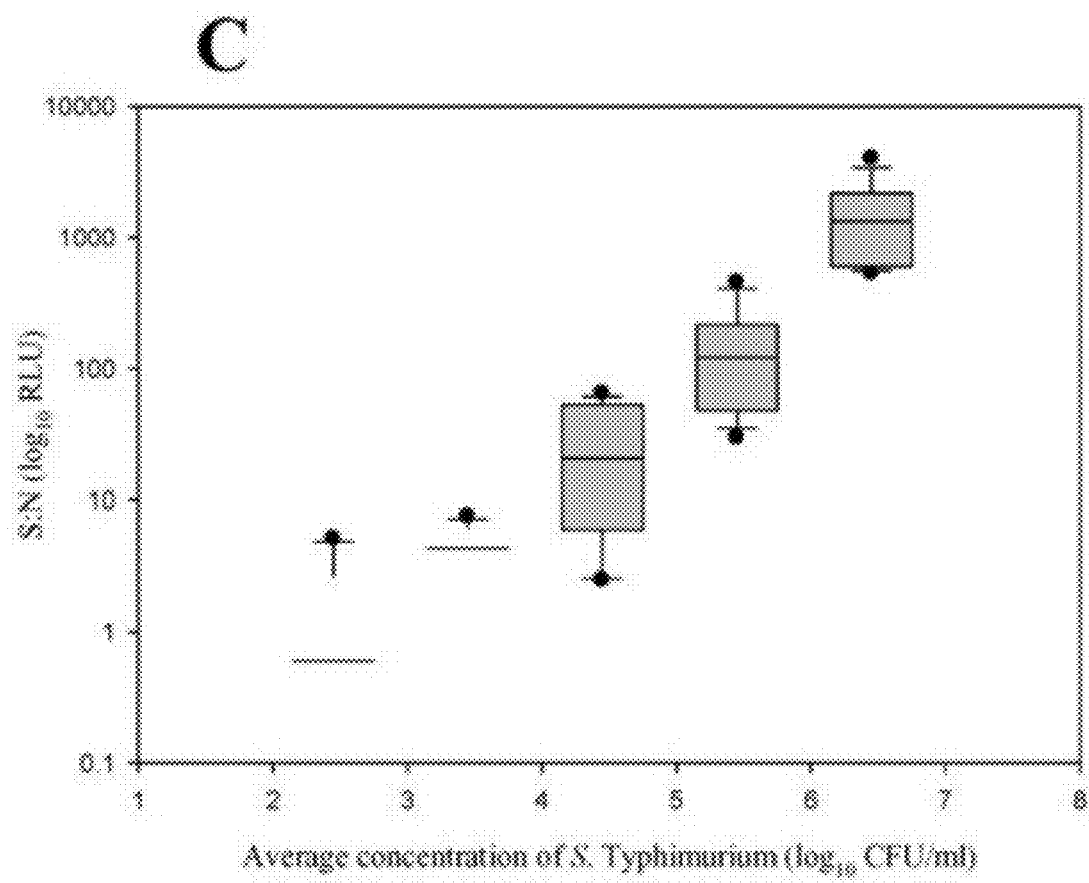
Figure 4:
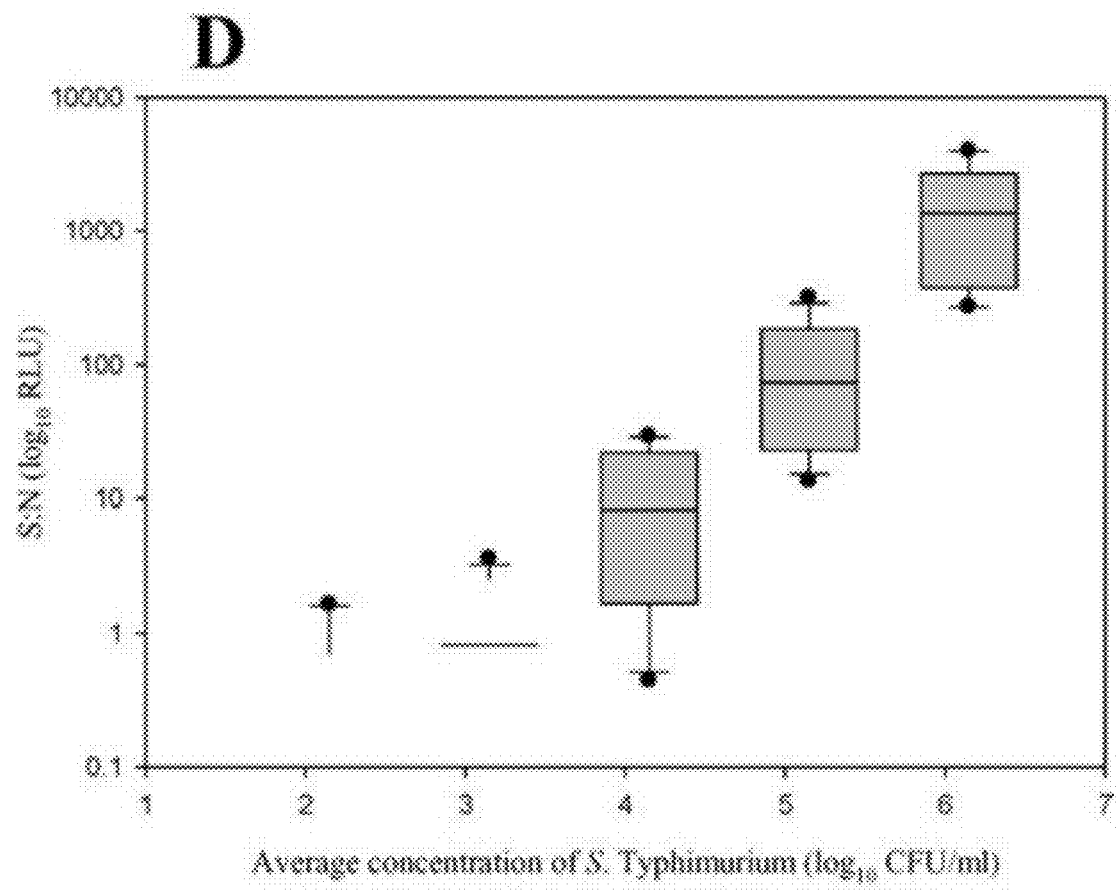
Figure 4:
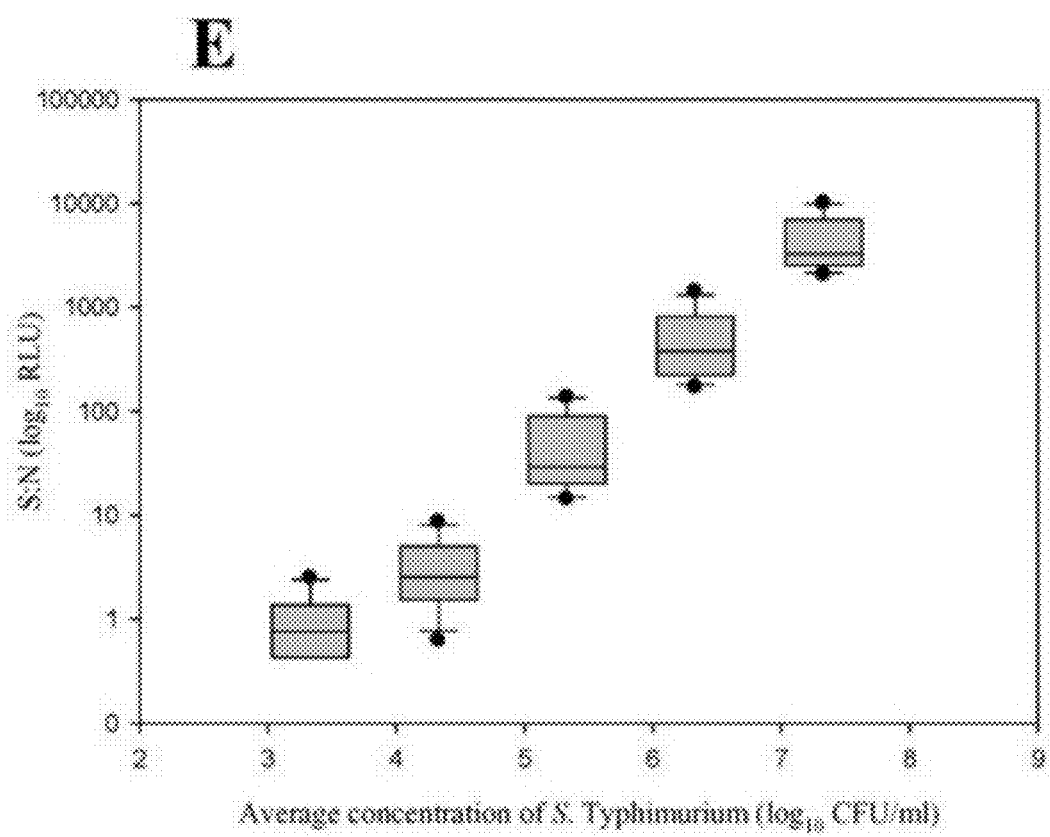
Figure 4:
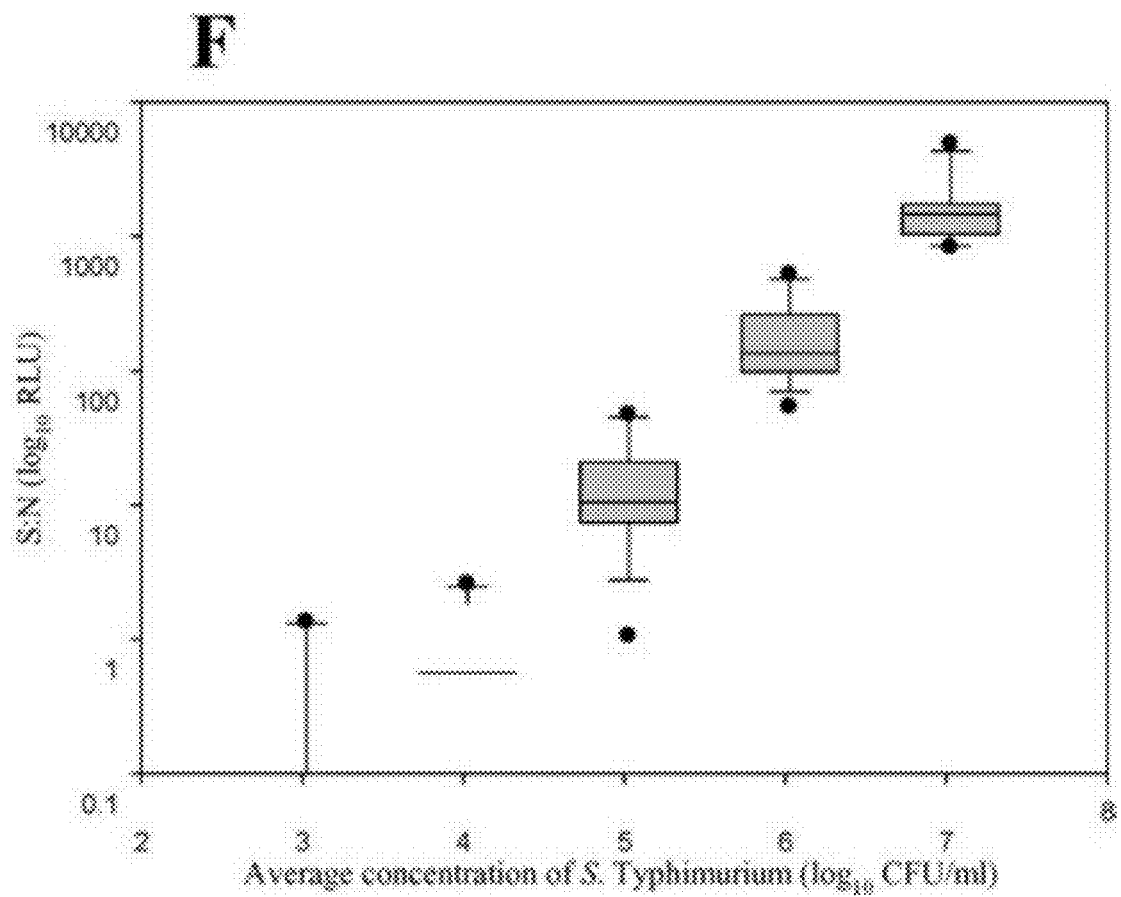

The LOD for $E.$ $coli$ O157:H7 in ground beef homogenate (n=14) was $9.42 \times 10^3$ CFU/ml for the target only (FIG. 3C) and $4.71 \times 10^4$ CFU/ml in mixed culture (FIG. 3D). The LOD for $Salmonella$ $Typhimurium$ in ground beef homogenate (n=15) was $6.28 \times 10^4$ CFU/ml for the target only (FIG. 4A) and $3.08 \times 10^5$ CFU/ml in mixed culture (FIG. 4B). There was no overlap of average S:N at concentrations>$10^4$ CFU/ml for either target. There was little variability at concentrations>$10^4$ CFU/ml, and similar variability was seen for the target only as for the target in mixed culture. S:N were significantly higher at all concentrations when comparing $E.$ $coli$ O157:H7 only to $E.$ $coli$ O157:H7 in mixed culture (P<0.0002 at all concentrations) and when comparing $Salmonella$ $Typhimurium$ only to $Salmonella$ $Typhimurium$ in mixed culture (in CFU per milliliter: $10^6$, P=0.0007; $10^5$, P=0.0003; $10^4$, P<0.0001; $10^3$, P=0.0264).

The LOD for $Salmonella$ $Typhimurium$ in apple juice (n=17) was $2.82 \times 10^3$ CFU/ml for the target only (FIG. 4C) and $1.41 \times 10^4$ CFU/ml in mixed culture (FIG. 4D). The LOD for $E.$ $coli$ O157:H7 in apple juice (n=16) was $8.78 \times 10^3$ CFU/ml for the target only (FIG. 3E) and $4.30 \times 10^4$ CFU/ml in mixed culture (FIG. 3F). S:N were more variable in this matrix, with overlap among ratios at all concentrations for $Salmonella$ $Typhimurium$ (but not $E.$ $coli$ O157:H7). There was no significant difference in S:N at any concentration except $10^3$ CFU/ml (which was just outside the confidence interval) when comparing apple juice containing $Salmonella$ $Typhimurium$ only to apple juice containing $Salmonella$ $Typhimurium$ in mixed culture. There was a significant difference in S:N when comparing $E.$ $coli$ O157:H7 only to $E.$ $coli$ O157:H7 in mixed culture at the two highest concentrations (in CFU per milliliter: $10^6$, P=0.0257; $10^5$, P=0.0387), but not at the two lowest concentrations. The P values at the two highest concentrations were just outside the confidence interval.

The LOD in milk (n=14) was $2.14 \times 10^4$ CFU/ml for *Salmonella Typhimurium* only (FIG. 4E) and $1.06 \times 10^5$ CFU/ml for *Salmonella Typhimurium* in mixed culture (FIG. 4F). There was no overlap of average S:N at concentrations $>10^4$ CFU/ml and low variability among both sets of data at all concentrations. There was a significant difference in S:N at all concentrations when comparing *Salmonella Typhimurium* only to *Salmonella Typhimurium* in mixed culture (in CFU per milliliter: $10^6$, P=0.0023; $10^5$, P=0.0007; $10^4$, P=0.0012; $10^3$, P=0.0022).

There was no significant difference in S:N across matrices for *E. coli* O157:H7 at any concentration for target cells only or in mixed culture. There was a significant difference in S:N for *Salmonella Typhimurium* across matrices for target cells only (P<0.005 at all concentrations) and for target cells in mixed culture (P<0.001 at all concentrations). However, there was no significant difference in S:N for target cells only in apple juice versus beef homogenate or in milk versus beef homogenate at the higher concentrations. A linear increase in signal with increasing cell concentration was observed within each matrix for targets alone and for targets in mixed culture, with $r^2$ values equal to or greater than 0.93 and P values less than 0.05. This linear correlation was observed across matrices. Specificity for live cells was assessed by ATP-BLIA via *Salmonella Typhimurium* and *E. coli* O157:H7 positive control (data not shown). S:N were less than 3.0 (the minimum cutoff for positive detection) for all concentrations ranging from $10^4$ (the lower limit of detection) to $10^7$ cells/ml (by direct count).

Subsequent evaluation of additional strains (data not shown) yielded the following results: detection of seven *E. coli* O157:H7 strains and one *E. coli* O157:NM at an average of $10^4$ CFU/ml in all matrices; and detection of six strains of *Salmonella Typhimurium* and four strains of *Salmonella Enteritidis* at an average of $10^5$ CFU/ml in all matrices. *Salmonella Choleraesuis* was detected at $10^5$ CFU/ml in ground beef homogenate and apple juice but was not detected in milk. Minimal cross-reactivity to related enterobacteria at high concentrations was observed.

Example IV

ATP-BLIA Plus PCR

Figure 5:
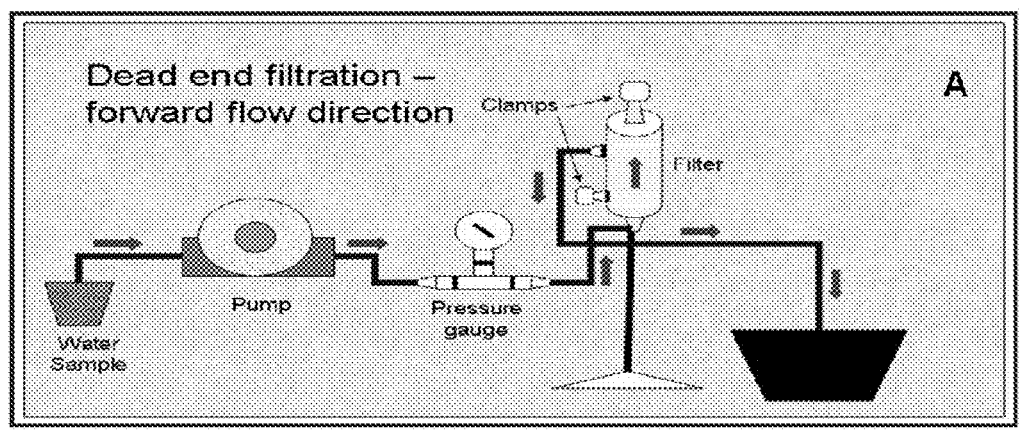
FIG. 5. Schematic of the recreational dead-end concentrator for sample collection (A) and sample elution (B) modes.
Figure 5:
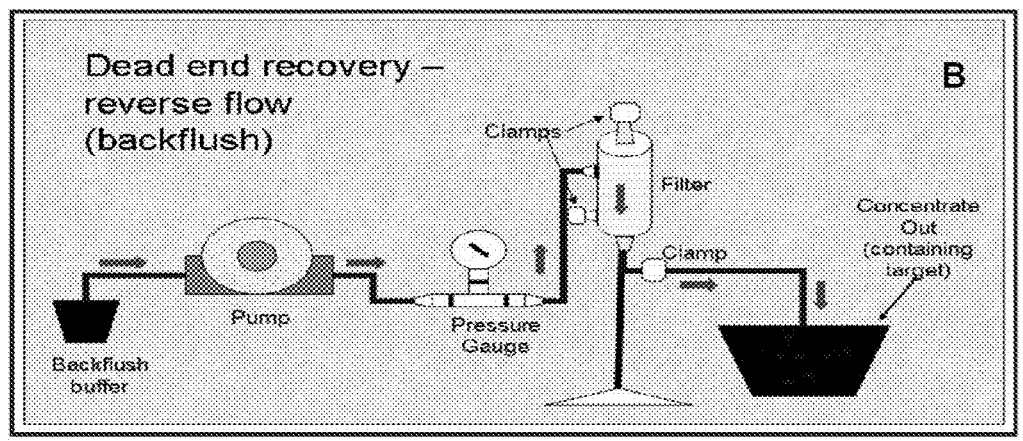

A 10 L sample of Hillsborough River water was spiked with raw sewage and concentrated by hollow fiber ultrafiltration (FIG. 5). The retentate was assessed for the presence of IOs and was then inoculated with target cells. Consecutive serial dilutions of inoculated retentate were incubated in the wells of a microtiter plate with specific antibodies immobilized on the surface. The specificity of the antibodies against common IOs was evaluated by ELISA prior to their use. Non-inoculated retentate was used to establish background. The plates were washed, and the wells were incubated with BacTiter-Glo reagent (Promega) in Mueller Hinton II broth. Bioluminescent output was measured on the GloMax 96 Luminometer (Promega) and signal-to-noise ratios were calculated. The plates were centrifuged and washed and the DNA was suspended in PBS for use in the PCR assay. The thermal cycling conditions for waterborne pathogen detection are shown in FIG. 6. Primer information can be found in Ke, D., F. J. Picard, F. Martineau, C. Menard, P. H. Roy, M. Ouellette, and M. G. Bergeron. 1999. Development of a PCR assay for rapid detection of enterococci. J. Clin. Microbiol. 37(11): 3497-3503; Kong, R. Y. C., S. K. Y. Lee, T. W. F. Law, S. H. W. Law, and R. S. S. Wu. 2002. Rapid detection of six types of bacterial pathogens in marine waters by multiplex PCR. Water Research. 36: 2801-2812; Leskinen, S. D. and D. V. Lim. 2008. Rapid ultrafiltration concentration and biosensor detection of enterococci from large volumes of Florida recreational water. Appl. Environ. Microbiol. 74(15): 4792-4798; and Osek, J. 2003. Development of a multiplex PCR approach for the identification of Shiga toxin-producing *Escherichia coli* strains and their major virulence factor genes. J. Appl. Microbiol. 95: 1217-1225.

Figure 7:
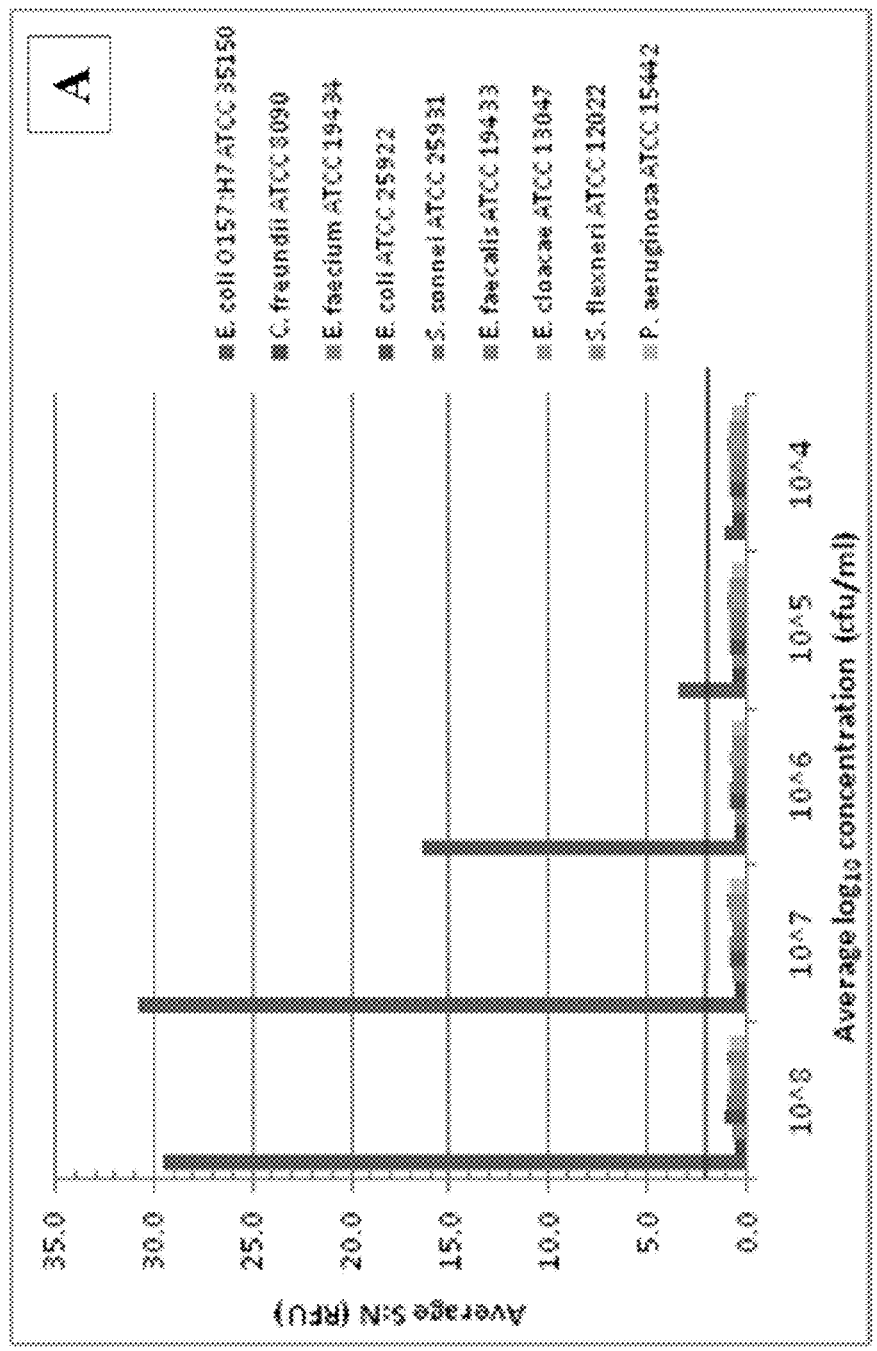
FIG. 7. ELISA detection of *E. coli* O157:H7 (A), *Shigella* spp. (B), and fecal enterococci (C). The x-axis displays average $\log_{10}$ concentrations in CFU/ml. Signal-to-noise ratios were determined by dividing the raw fluorescence by the average background flourescence. Triplicate S:N from triplicate plates were averaged and standard deviations were calculated. Average S:N≥2.0 were considered positive.
Figure 7:
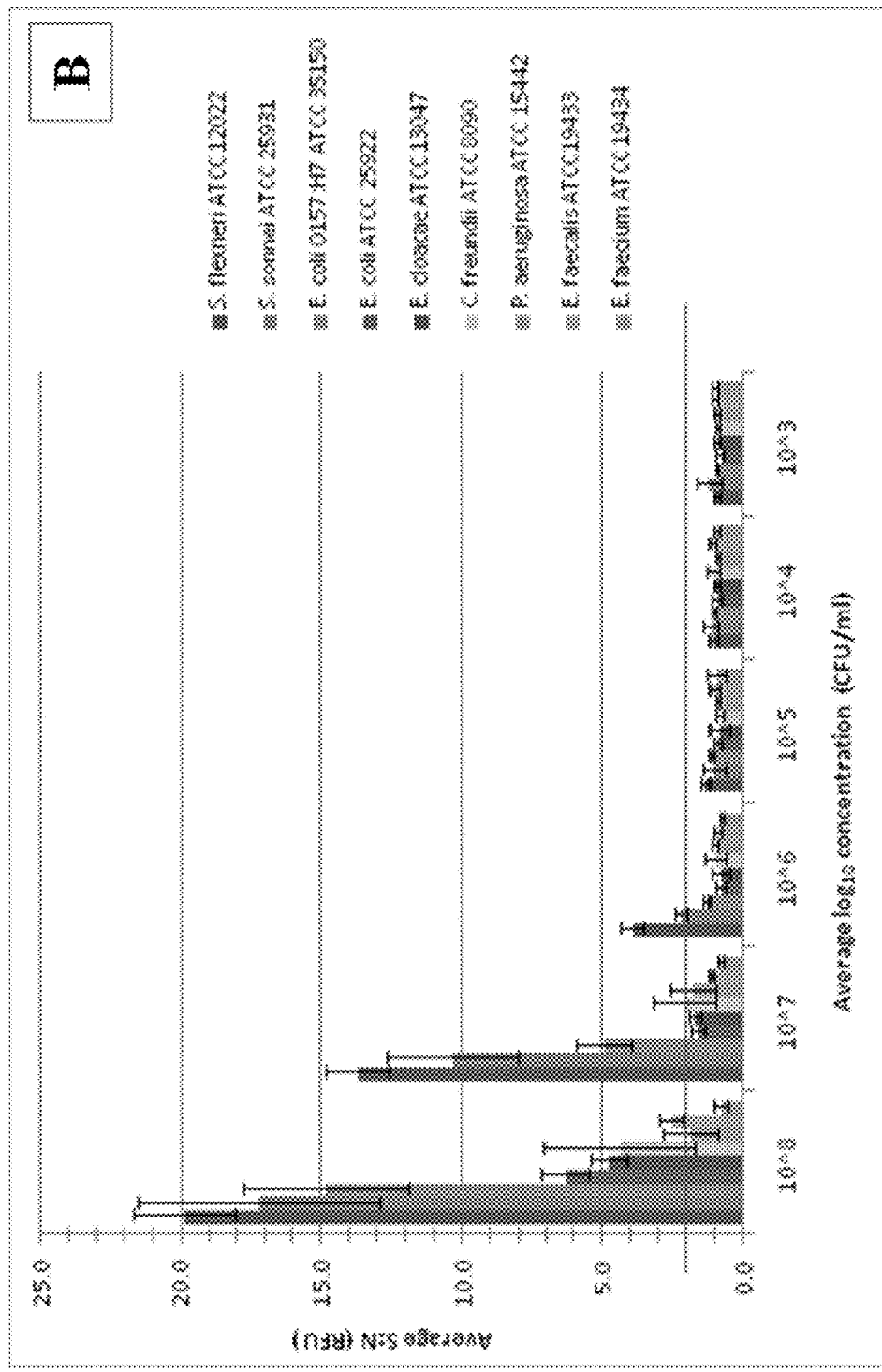
Figure 7:
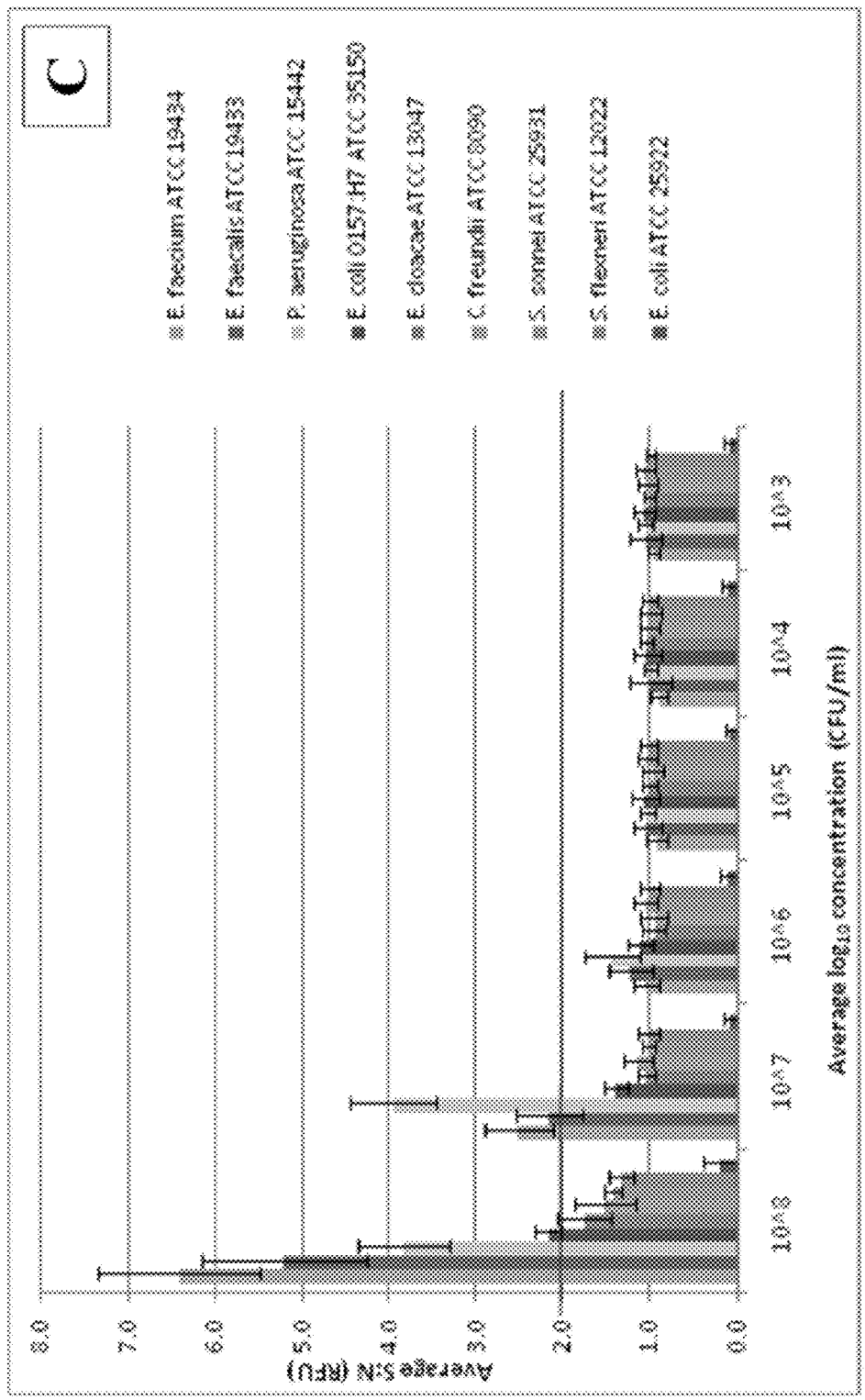
Figure 8:
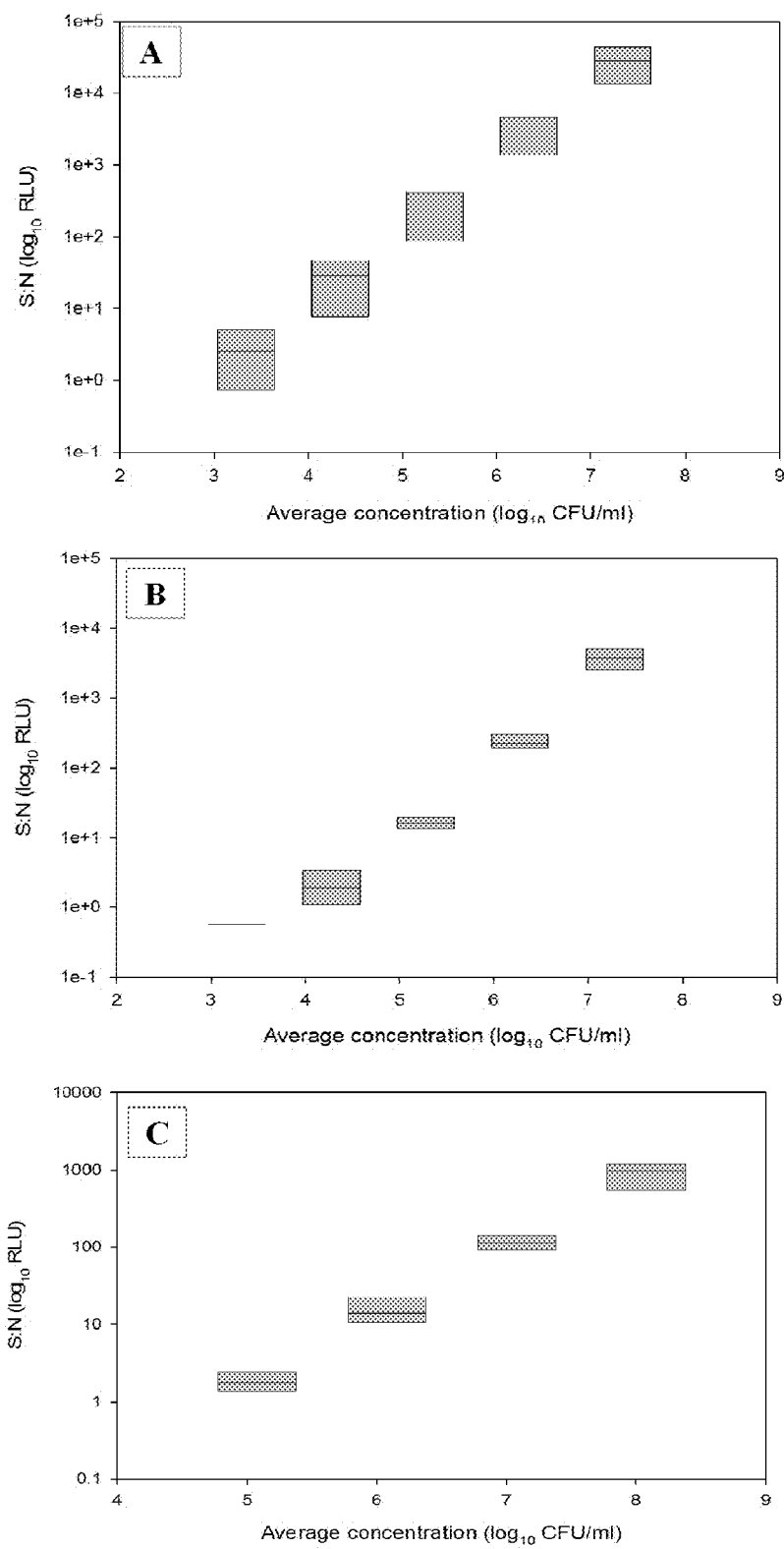
FIG. 8. ATP-bioluminescence immunoassay detection of *E. coli* O157:H7 (A), *Shigella sonnei* (B), and entereococci (C). Graphs are on a $\log_{10}$ scale. Signal-to-noise ratios (S:N) are the sample average minus the average background divided by the standard deviation of the background. Samples were considered positive for a S:N ratio≥3. Each box displays the median (center line) S:N and the $25^{th}$ and $75^{th}$ percentiles (lower and upper box limits, respectively).

The ATP-BLIA resulted in limits of detection of $10^4$ CFU/ml for *E. coli* O157:H7, and $10^5$ CFU/ml for *S. sonnei* and enterococci (see FIGS. 7-9). The average concentration of each bacterium in retentate was evaluated by viable counts on selective media. A strong linear correlation was observed between the average CFU/ml and bioluminescent output over four orders of magnitude for *E. coli* O157:H7 ($r^2$=0.942), *S. sonnei* ($r^2$=0.949), and enterococci ($r^2$=0.947). Detection was not affected by the presence of fecal coliforms ($4.5 \times 10^4$ CFU/ml) or *E. coli* ($4.2 \times 10^4$ CFU/ml) in the retentate. The presence of all three targets was confirmed by PCR. Concentration, immunoassay detection, and PCR were completed in 4 hours. This method resulted in timely, specific detection and quantification of target bacteria in recreational water samples.

Example V

Comparison of Detection by ATP-Bioluminescence after Different Immunocapture Methods The objective of this example was to determine whether detection via ATP-bioluminescence after IMS is possible and to evaluate this method against detection after target capture using immobilized antibody. The target in these assays is *E. coli* O157:H7, although assays are contemplated using *S. aureus*.

Figure 10:
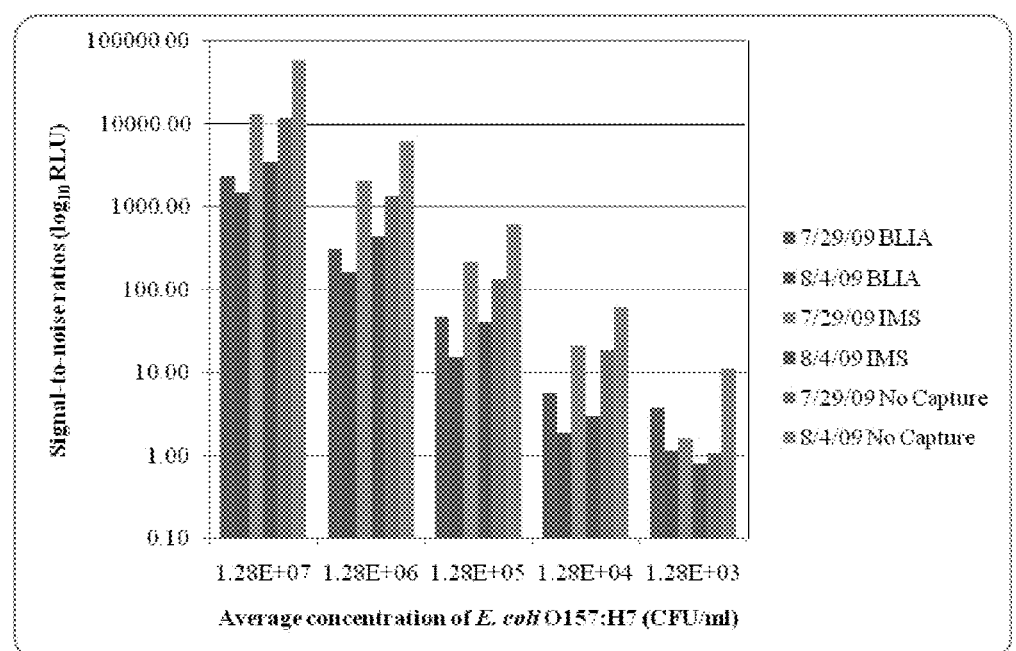
FIG. 10. Graphical representation of data reported in Tables 2 and 3.

As used in this example (including Tables 2-3 and FIG. 10):

"BLIA" refers to capture and identification of *E. coli* O157:H7 using *E. coli* O157:H7 antibody coated on the wells of a microtiter plate, followed by viability determination using ATP-bioluminescence.

"IMS" refers to capture and identification of *E. coli* O157:H7 using *E. coli* O157:H7 antibody-coated immunomagnetic beads; the bead-antibody-target complex is added to the wells of a microtiter plate and viability is determined using ATP-bioluminescence.

"No capture" refers to the positive control, which is *E. coli* O157:H7 serially diluted in PBS and added to the wells of a microtiter plate. No antibody capture is involved. Viability is also determined using ATP-bioluminescence.

The initial results were comparable for both immunocapture methods. On Jul. 29, 2009, $10^6$ CFU/ml of the highest concentration was recovered by IMS, which means $10^5$ CFU/ml was run in the assay. The concentration used for the BLIA was $10^6$ CFU/ml; assuming less than 100% capture with immobilized antibody, the actual amount detected would be in the $10^5$ CFU/ml range. The signals in line 1 of Table 2 are in the same log which correlates to the same concentration of cells. The same concept is evident in Table 3 (Aug. 4, 2009). By comparison, IMS captured high $10^6$ (almost $10^7$) CFU/ml, which means nearly $10^6$ CFU/ml was run in the assay. Correspondingly, the S:N are one log higher.

TABLE 2

Detection of *E. coli* O157:H7 after capture, comparison of methods on Jul. 29, 2009.

| BLIA | | IMS | | | No Capture | |
|---|---|---|---|---|---|---|
| | | CFU/ml | CFU/ml | | | |
| CFU/ml | S:N | Start | Recovered | S:N | CFU/ml | S:N |
| 1.37E+07 | 1493.28 | 1.37E+07 | 1.16E+06 | 3529.33 | 2.04E+07 | 58493.56 |
| 1.37E+06 | 160.53 | 1.37E+06 | 1.51E+05 | 439.63 | 2.04E+06 | 6141.84 |
| 1.37E+05 | 15.57 | 1.37E+05 | 1.42E+04 | 40.87 | 2.04E+05 | 614.58 |
| 1.37E+04 | 1.87 | 1.37E+04 | 9.78E+02 | 3.02 | 2.04E+04 | 61.22 |
| 1.37E+03 | 1.13 | 1.37E+03 | 1.96E+02 | 0.81 | 2.04E+03 | 11.28 |

S:N are in average RLU.

TABLE 3

Detection of *E. coli* O157:H7 after capture, comparison of methods on Aug. 4, 2009.

| BLIA | | IMS | | | No capture | |
|---|---|---|---|---|---|---|
| | | CFU/ml | CFU/ml | | | |
| CFU/ml | S:N | Start | Recovered | S:N | CFU/ml | S:N |
| 1.19E+07 | 2335.94 | 1.19E+07 | 9.43E+06 | 13020.23 | 1.93E+07 | 11809.79 |
| 1.19E+06 | 307.38 | 1.19E+06 | 1.64E+06 | 2072.44 | 1.93E+06 | 1341.98 |
| 1.19E+05 | 46.98 | 1.19E+05 | 1.65E+05 | 213.14 | 1.93E+05 | 133.59 |
| 1.19E+04 | 5.63 | 1.19E+04 | 1.41E+04 | 21.24 | 1.93E+04 | 18.56 |
| 1.19E+03 | 3.75 | 1.19E+03 | 1.55E+03 | 1.59 | 1.93E+03 | 1.08 |

S:N are in average RLU.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense. Any materials, which may be cited above, are fully incorporated herein by reference.

It is also to be understood that the following claims are intended to cover all of the generic and specific features of the invention herein described, and all statements of the scope of the invention which, as a matter of language, might be said to fall therebetween. Relative terminology, such as "substantially" or "about," describe the specified materials, steps, parameters or ranges as well as those that do not materially affect the basic and novel characteristics of the claimed inventions as whole (as would be appreciated by one of ordinary skill in the art). Now that the invention has been described,

What is claimed is:

1. A kit for use in an ATP bioluminescence immunoassay (ATP-BLIA) for the rapid detection and quantification of specific viable pathogenic cells in a complex sample without requiring previous enrichment of the sample to remove contaminants, comprising:
 a pre-coated vessel having at least one detection well coated with a capture antibody;
 a wash solution;
 a blocking buffer;
 a general purpose broth solution wherein the broth solution is not used for prior enrichment of the sample;
 a bioluminescence reagent comprised of an ATP extracting agent and a luciferase enzyme; and
 instructions for detecting the specific viable pathogenic cells in the complex sample without requiring previous enrichment of the sample to remove contaminants.

2. The kit of claim 1, wherein the capture antibody is specific for a pathogen selected from the group consisting of *E. coli*, *Salmonella Typhimurium*, *Shigella sonnei*, *Streptococcus* and enterococci.

3. The kit of claim 2, wherein the capture antibody is selected from the group consisting of goat polyclonal antibody to *E. coli* and rabbit polyclonal antibody to *Salmonella*.

4. The kit of claim 1, wherein the pre-coated vessel is a 96-well plate.

5. The kit of claim 1, wherein the wash solution is comprised of phosphate buffered saline and a non-ionic surfactant.

6. The kit of claim 1, wherein the blocking buffer is comprised of equal parts casein and bovine serum albumin in phosphate buffered saline.

7. The kit of claim 1, wherein the broth solution is Mueller Hinton II broth.

8. The kit of claim 1, wherein the instructions comprise the steps of:
 adding the blocking buffer to the at least one detection well;
 adding the complex sample to the at least one detection well;
 washing the pre-coated vessel with the wash solution to remove a portion of the complex sample which does not contain immobilized antibody targets;

adding the broth solution to the at least one detection well;
adding the bioluminescence agent to the at least one detection well; and
using a luminometer to detect the specific viable pathogenic cells in the complex sample by measuring luminescent output from the pre-coated vessel.

* * * * *